(12) United States Patent
Hartmann et al.

(10) Patent No.: US 9,738,583 B2
(45) Date of Patent: Aug. 22, 2017

(54) PROCESS FOR PREPARING ACRYLIC ACID

(71) Applicant: BASF SE, Ludwigshafen am Rhein (DE)

(72) Inventors: Marco Hartmann, Jockgrim (DE); Lukas Schulz, Mannheim (DE); Nicolai Tonio Woerz, Darmstadt (DE); Yong Liu, Shanghai (CN); Till Christian Brueggemann, Ludwigshafen (DE); Michael Lejkowski, Neckargemuend (DE); Johannes Lieberknecht, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/348,130

(22) Filed: Nov. 10, 2016

(65) Prior Publication Data

US 2017/0129840 A1 May 11, 2017

Related U.S. Application Data

(60) Provisional application No. 62/253,702, filed on Nov. 11, 2015.

(30) Foreign Application Priority Data

Nov. 11, 2015 (DE) .......................... 10 2015 222 196

(51) Int. Cl.
*C07C 51/353* (2006.01)
(52) U.S. Cl.
CPC ................... *C07C 51/353* (2013.01)

(58) Field of Classification Search
CPC .................................................... C07C 51/353
See application file for complete search history.

(56) References Cited

U.S. PATENT DOCUMENTS 4,792,620 A * 12/1988 Paulik ................. B01J 31/0231
560/232
2013/0085292 A1 4/2013 Mueller et al.
2014/0066651 A1 * 3/2014 Mueller ................ C07C 51/353
562/599

FOREIGN PATENT DOCUMENTS

WO WO 2014/184098 A1 11/2014

OTHER PUBLICATIONS

Norskov et al, Nature Chemistry, Towards the Computational Design of Solid Catalysts, 2009, 1, pp. 37-46.*

* cited by examiner

*Primary Examiner* — Paul A Zucker
(74) *Attorney, Agent, or Firm* — Oblon, McClelland, Maier & Neustadt, L.L.P.

(57) ABSTRACT

A process for preparing acrylic acid from formaldehyde and acetic acid, is performed by (i) providing a gaseous stream S1 comprising formaldehyde, acetic acid, oxygen and water, where the formaldehyde content of stream S1 is in the range from 8% to 18% by volume, based on the total volume of stream S1, the ratio of the volumes of acetic acid to formaldehyde is in the range from 0.6:1 to 1.1:1, and the molar ratio of oxygen to the total amount of organic carbon is in the range from 0.02:1 to 0.15:1; and (ii) contacting stream S1 with an aldol condensation catalyst in a reaction zone to obtain a gaseous stream S2 containing acrylic acid.

12 Claims, 1 Drawing Sheet

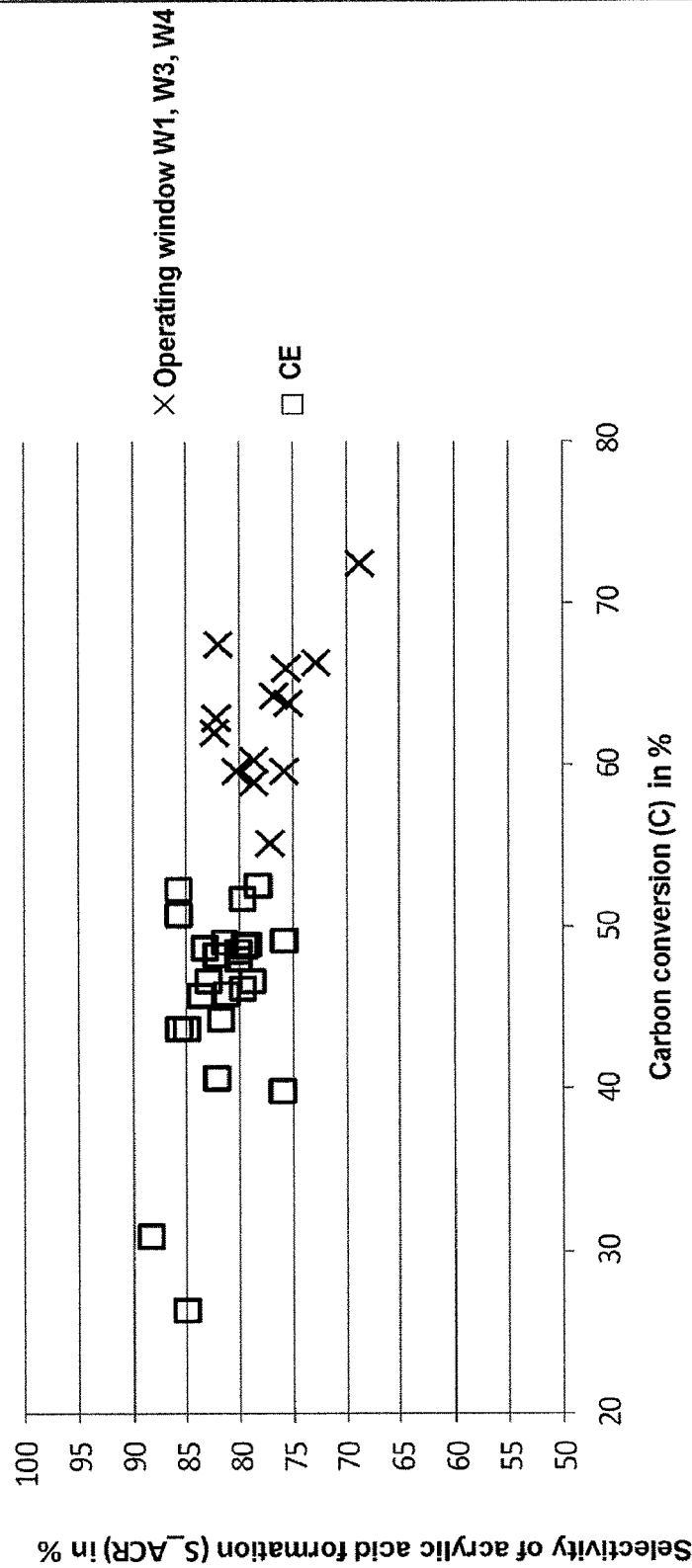

PROCESS FOR PREPARING ACRYLIC ACID

The present invention relates to a process for preparing acrylic acid from formaldehyde and acetic acid, in which a defined combination of parameter ranges is used to optimize selectivity of acrylic acid formation and conversion.

Acrylic acid, an important monomer for production of homo- and copolymers, is typically obtained by a heterogeneously catalyzed two-stage partial oxidation proceeding from propene, with acrolein as intermediate.

A possible alternative is the preparation of acrylic acid in a heterogeneously catalyzed gas phase reaction by a condensation of formaldehyde and acetic acid. In such an aldol condensation, various parameters such as the ratio of reactants to products, the ratio of reactants to one another, the temperature at which the reactants are reacted or the choice of catalyst play an important role.

Various catalysts have been described to date, each of which effectively catalyzes the necessary aldol condensation between formaldehyde and acetic acid under very specific conditions. Although ranges in which the aldol condensation to give acrylic acid can be conducted are specified for individual parameters, for example the temperature, the individual parameters are considered in isolation from one another.

The object underlying the present invention was therefore that of providing a novel process, especially one performable advantageously on the industrial scale, for preparing acrylic acid by means of aldol condensation of formaldehyde and acetic acid, in which a wide variety of different catalysts can be used.

It has been found that, surprisingly, such a process can be implemented by combining defined parameter ranges with one another, resulting in formation of what is called an operating window.

BRIEF DESCRIPTION OF THE DRAWINGS

FIG. 1 shows the selectivity of acrylic acid formation in % (ordinate, 50% to 100%) versus the carbon conversion (C) in % (abscissa, 20% to 80%) for inventive operating windows according to table 7.

The present invention therefore relates to a process for preparing acrylic acid from formaldehyde and acetic acid, comprising
  (i) providing a gaseous stream S1 comprising formaldehyde, acetic acid, oxygen and water,
    where the formaldehyde content of stream S1 is in the range from 8% to 18% by volume, based on the total volume of stream S1,
    the ratio of the volumes of acetic acid to formaldehyde is in the range from 0.6:1 to 1.1:1, and
    the molar ratio of oxygen to the total amount of organic carbon is in the range from 0.02:1 to 0.15:1;
  (ii) contacting stream S1 with an aldol condensation catalyst in a reaction zone to obtain a gaseous stream S2 comprising acrylic acid.

In the context of the present invention, the molar ratio of oxygen to the total amount of organic carbon is also referred to as "$O_2$/TOC".

The process of the invention enables achievement of a higher selectivity with respect to acrylic acid formation when the reaction is run within the ranges for the three parameters mentioned (formaldehyde content of stream S1; ratio of the volumes of acetic acid to formaldehyde; molar ratio of oxygen to the total amount of organic carbon).

The combination of the ranges for the three parameters in stream S1 of formaldehyde content of stream S1, ratio of the volumes of acetic acid to formaldehyde and molar ratio of oxygen to the total amount of organic carbon is also referred to as operating window.

Preferably, the process of the invention additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

Preferably, the ratio of the volumes of formaldehyde to water in stream S1 is in the range from 0.5:1 to 1.5:1, further preferably in the range from 0.6:1 to 1.3:1.

The space velocity GHSV in the context of this invention is defined as the total volume flow rate of stream S1, in $m^3/h$, per unit catalyst volume, in $m^3$, under standard conditions, i.e. at a temperature of 0° C. and absolute pressure 1.013 bar. The catalyst volume is defined as the bed volume, i.e. the catalyst-filled volume of the reactor. Preferably, the space velocity GHSV in the reaction zone is in the range from 800 to 6500 $h^{-1}$.

The temperature in the reaction zone, in the context of this invention, is defined as the temperature at which stream S1 is contacted with the aldol condensation catalyst. Preferably, the temperature in the reaction zone is in the range from 350 to 400° C.

Further preferably, the process of the present invention comprises a combination of the six parameter ranges of formaldehyde content of stream S1 in the range from 8% to 18% by volume, based on the total volume of stream S1, ratio of the volumes of acetic acid to formaldehyde in the range from 0.6:1 to 1.1:1, molar ratio of oxygen to the total amount of organic carbon in the range from 0.02:1 to 0.15:1, ratio of the volumes of formaldehyde to water in stream S1 in the range from 0.5:1 to 1.5:1, space velocity GHSV in the reaction zone in the range from 800 to 6500 $h^{-1}$, and temperature in the reaction zone in the range from 350 to 400° C.

Preferably, the process of the invention for preparing acrylic acid from formaldehyde and acetic acid therefore comprises
  (i) providing a gaseous stream S1 comprising formaldehyde, acetic acid, oxygen and water,
  (ii) contacting stream S1 with an aldol condensation catalyst in a reaction zone to obtain a gaseous stream S2 comprising acrylic acid,
where the formaldehyde content of stream S1 is in the range from 8% to 18% by volume, based on the total volume of stream S1, the ratio of the volumes of acetic acid to formaldehyde is in the range from 0.6:1 to 1.1:1, the molar ratio of oxygen to the total amount of organic carbon is in the range from 0.02:1 to 0.15:1, the ratio of the volumes of formaldehyde to water in stream S1 is in the range from 0.5:1 to 1.5:1, the space velocity GHSV in the reaction zone is in the range from 800 to 6500 $h^{-1}$ and the temperature in the reaction zone is in the range from 350 to 400° C.

Operating Window 1

In a first preferred configuration of the process of the invention, the formaldehyde content of stream S1 is further preferably in the range from 8% to 14% by volume, based on the total volume of stream S1.

In this first preferred configuration, the ratio of the volumes of acetic acid to formaldehyde in stream S1 is in the range from 0.9:1 to 1.1:1.

In this first preferred configuration, the molar ratio of oxygen to the total amount of organic carbon ($O_2$/TOC) is in the range from 0.02:1 to 0.15:1.

In this first preferred configuration, the combination of the ranges for three parameters in stream S1 of formaldehyde content of stream S1, ratio of the volumes of acetic acid to formaldehyde and molar ratio of oxygen to the total amount of organic carbon is also referred to as operating window 1.

The present invention therefore relates, in this first preferred configuration, preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.9:1 to 1.1:1, and the molar ratio of oxygen to the total amount of organic carbon is in the range from 0.02:1 to 0.15:1.

Preferably, the process of the invention in this first preferred configuration, i.e. operating window 1 as well, additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

In this first preferred configuration, the ratio of the volumes of formaldehyde to water in stream S1 is further preferably in the range from 0.8:1 to 1.3:1.

In this first preferred configuration, the space velocity GHSV in the reaction zone is further preferably in the range from 800 to 2600 $h^{-1}$.

In this first preferred configuration, the temperature in the reaction zone is further preferably in the range from 360 to 380° C.

In this first preferred configuration of the process of the present invention, it is further preferable that the formaldehyde content of stream S1 is in the range from 8% to 14% by volume, based on the total volume of stream S1, the ratio of the volumes of acetic acid to formaldehyde in stream S1 is in the range from 0.9:1 to 1.1:1, the molar ratio of oxygen to the total amount of organic carbon is in the range from 0.02:1 to 0.15:1, the ratio of the volumes of formaldehyde to water is in the range from 0.8:1 to 1.3:1, the space velocity GHSV in the reaction zone is in the range from 800 to 2600 $h^{-1}$ and the temperature in the reaction zone is in the range from 360 to 380° C.

The present invention therefore relates, in this first preferred configuration, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.9:1 to 1.1:1, the molar ratio of oxygen to the total amount of organic carbon is in the range from 0.02:1 to 0.15:1, the ratio of the volumes of formaldehyde to water is in the range from 0.8:1 to 1.3:1, the space velocity GHSV in the reaction zone is in the range from 800 to 2600 $h^{-1}$ and the temperature in the reaction zone is in the range from 360 to 380° C.

Operating Window 2

In a second preferred configuration of the process of the invention, the formaldehyde content of stream S1 is further preferably in the range from 15% to 18% by volume, based on the total volume of stream S1.

In this second preferred configuration, the ratio of the volumes of acetic acid to formaldehyde in stream S1 is further preferably in the range from 0.75:1 to 1.1:1.

In this second preferred configuration, the molar ratio of oxygen to the total amount of organic carbon (02/TOC) is in the range from 0.02:1 to 0.15:1.

In this second preferred configuration, the combination of the ranges for three parameters in stream S1 of formaldehyde content of stream S1, ratio of the volumes of acetic acid to formaldehyde and molar ratio of oxygen to the total amount of organic carbon is also referred to as operating window 2.

The present invention therefore relates, in this second preferred configuration, preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 15% to 18% by volume, based on the total volume of stream S1, the ratio of the volumes of acetic acid to formaldehyde in stream S1 is in the range from 0.75:1 to 1.1:1, and the molar ratio of oxygen to the total amount of organic carbon in stream S1 is in the range from 0.02:1 to 0.15:1.

Preferably, the process of the invention in this second preferred configuration, i.e. operating window 2 as well, additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

In this second preferred configuration, the ratio of the volumes of formaldehyde to water in stream S1 is further preferably in the range from 0.8:1 to 1.3:1.

In this second preferred configuration, the space velocity GHSV in the reaction zone is further preferably in the range from 800 to 1600 $h^{-1}$.

In this second preferred configuration, the temperature in the reaction zone is further preferably in the range from 350 to 390° C.

In this second preferred configuration of the process of the present invention, it is further preferable that the formaldehyde content of stream S1 is in the range from 15% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the GHSV in the reaction zone is in the range from 800 to 1600 $h^{-1}$ and the temperature in the reaction zone is in the range from 350 to 390° C.

The present invention therefore relates, in this second preferred configuration, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 15% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the GHSV in the reaction zone is in the range from 800 to 1600 $h^{-1}$ and the temperature in the reaction zone is in the range from 350 to 390° C.

Operating Window 3

In a third preferred configuration of the process of the invention, the formaldehyde content of stream S1 is in the range from 8% to 18% by volume, based on the total volume of stream S1.

In this third preferred configuration, the ratio of the volumes of acetic acid to formaldehyde in stream S1 is further preferably in the range from 0.75:1 to 1.1:1.

In this third preferred configuration, the molar ratio of oxygen to the total amount of organic carbon ($O_2$/TOC) is in the range from 0.02:1 to 0.15:1.

In this third preferred configuration, the combination of the ranges for three parameters in stream S1 of formaldehyde content of stream S1, ratio of the volumes of acetic acid to formaldehyde and molar ratio of oxygen to the total amount of organic carbon is also referred to as operating window 3.

The present invention therefore relates, in this third preferred configuration, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 18% by volume, based on the total volume of stream S1, the ratio of the volumes of acetic acid to formaldehyde in stream S1 is in the range from 0.75:1 to 1.1:1, and the molar ratio of oxygen to the total amount of organic carbon in stream S1 is in the range from 0.02:1 to 0.15:1.

Preferably, the process of the invention in this third preferred configuration, i.e. operating window 3 as well, additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

In this third preferred configuration, the ratio of the volumes of formaldehyde to water in stream S1 is further preferably in the range from 0.8:1 to 1.3:1.

In this third preferred configuration, the space velocity GHSV in the reaction zone is further preferably in the range from 1600 to 6500 $h^{-1}$.

In this third preferred configuration, the temperature in the reaction zone is further preferably in the range from 380 to 400° C.

In this third preferred configuration of the process of the present invention, it is further preferable that the formaldehyde content of stream S1 is in the range from 8% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the space velocity GHSV in the reaction zone is in the range from 1600 to 6500 $h^{-1}$ and the temperature in the reaction zone is in the range from 380 to 400° C.

The present invention therefore relates, in this third preferred configuration, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the space velocity GHSV in the reaction zone is in the range from 1600 to 6500 $h^{-1}$ and the temperature in the reaction zone is in the range from 380 to 400° C.

Operating Window 4

In a fourth preferred configuration of the process of the invention, the formaldehyde content of stream S1 is further preferably in the range from 8% to 14% by volume, based on the total volume of stream S1.

In this fourth preferred configuration, the ratio of the volumes of acetic acid to formaldehyde in stream S1 is further preferably in the range from 0.75:1 to 1.1:1.

In this fourth preferred configuration, the molar ratio of oxygen to the total amount of organic carbon ($O_2$/TOC) is in the range from 0.02:1 to 0.15:1.

In this fourth preferred configuration, the combination of the ranges for three parameters in stream S1 of formaldehyde content of stream S1, ratio of the volumes of acetic acid to formaldehyde and molar ratio of oxygen to the total amount of organic carbon is also referred to as operating window 4.

The present invention therefore relates, in this fourth preferred configuration, preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.75:1 to 1.1:1, and the molar ratio of oxygen to the total amount of organic carbon in stream S1 is in the range from 0.02:1 to 0.15:1.

Preferably, the process of the invention in this fourth preferred configuration, i.e. operating window 4 as well, additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

In this fourth preferred configuration, the ratio of the volumes of formaldehyde to water in stream S1 is in the range from 0.6:1 to 1.3:1.

In this fourth preferred configuration, the space velocity GHSV in the reaction zone is further preferably in the range from 800 to 1600 $h^{-1}$.

In this fourth preferred configuration, the temperature in the reaction zone is further preferably in the range from 350 to 360° C.

In this fourth preferred configuration of the process of the present invention, it is further preferable that the formaldehyde content of stream S1 is in the range from 8% to 14% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 1.3:1, the space velocity GHSV in the reaction zone is in the range from 800 to 1600 $h^{-1}$ and the temperature in the reaction zone is in the range from 350 to 360° C.

The present invention therefore relates, in this fourth preferred configuration, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 1.3:1, the space velocity GHSV in the reaction zone is in the range from 800 to 1600 $h^{-1}$ and the temperature in the reaction zone is in the range from 350 to 360° C.

Operating Window 5

In a fifth preferred embodiment of the process of the invention, the formaldehyde content of stream S1 is further preferably in the range from 8% to 14% by volume, based on the total volume of stream S1.

In this fifth preferred embodiment, the ratio of the volumes of acetic acid to formaldehyde in stream S1 is further preferably in the range from 0.66:1 to 1.1:1.

In this fifth preferred embodiment, the molar ratio of oxygen to the total amount of organic carbon ($O_2$/TOC) is in the range from 0.02:1 to 0.15:1.

In this fifth preferred embodiment, the combination of the ranges for three parameters in stream S1 of formaldehyde content of stream S1, ratio of the volumes of acetic acid to formaldehyde and molar ratio of oxygen to the total amount of organic carbon is also referred to as operating window 5.

The present invention therefore relates, in this fifth preferred embodiment, preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.66:1 to 1.1:1, and the molar ratio of oxygen to the total amount of organic carbon in stream S1 is in the range from 0.02:1 to 0.15:1.

Preferably, the process of the invention in this fifth preferred embodiment, i.e. operating window 5 as well, additionally comprises at least one further parameter range, further preferably at least two, further preferably three parameter ranges, where the parameters are selected from the group consisting of ratio of the volumes of formaldehyde to water in stream S1, space velocity GHSV in the reaction zone, and temperature in the reaction zone.

In this fifth preferred embodiment, the ratio of the volumes of formaldehyde to water in stream S1 is in the range from 0.6:1 to 0.79:1.

In this fifth preferred embodiment, the space velocity GHSV in the reaction zone is further preferably in the range from 800 to 1600 $h^{-1}$.

In this fifth preferred embodiment, the temperature in the reaction zone is further preferably in the range from 360 to 380° C.

In this fifth preferred embodiment of the process of the present invention, it is further preferable that the formaldehyde content of stream S1 is in the range from 8% to 14% by volume, based on the total volume of stream S1, the ratio of the volumes of acetic acid to formaldehyde in stream S1 is in the range from 0.66:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 0.79:1, the GHSV in the reaction zone is in the range from 800 to 1600 $h^{-1}$ and the temperature in the reaction zone is in the range from 360 to 380° C.

The present invention therefore relates, in this fifth preferred embodiment, further preferably to a process for preparing acrylic acid from formaldehyde and acetic acid, comprising
(i) providing a gaseous stream S1 comprising formaldehyde, acetic acid, oxygen and water,
(ii) contacting stream S1 with an aldol condensation catalyst in a reaction zone to obtain a gaseous stream S2 comprising acrylic acid,
where the formaldehyde content of stream S1 is in the range from 8% to 14% by volume, based on the total volume of stream S1, the ratio of the volumes of acetic acid to formaldehyde in stream S1 is in the range from 0.66:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 0.79:1, the GHSV in the reaction zone is in the range from 800 to 1600 $h^{-1}$ and the temperature in the reaction zone is in the range from 360 to 380° C.

Stream S1

The gaseous stream S1 provided in (i) comprises formaldehyde, acetic acid, oxygen and water. It is conceivable in principle that stream S1 consists of formaldehyde, acetic acid, oxygen and water.

Useful sources for the acetic acid in principle include any suitable source comprising at least a proportion of acetic acid. This may be acetic acid fed fresh to the process. It may likewise be acetic acid which has not been converted in the above-described process and which, for example after removal from the product stream in one or more workup steps, is recycled into the process. A combination of acetic acid fed fresh to the process and acetic acid recycled into the process is likewise possible. It is likewise possible to use acetic acid adducts, for example acetic anhydride.

Useful sources for the formaldehyde likewise in principle include any suitable source comprising at least a proportion of formaldehyde. This may be formaldehyde fed fresh to the process. It may likewise be formaldehyde which has not been converted in the above-described process and which, for example after removal from the product stream in one or more workup steps, is recycled into the process. A combination of formaldehyde fed fresh to the process and formaldehyde recycled into the process is likewise possible. For example, the source used for the formaldehyde may be an aqueous formaldehyde solution (formalin). It is likewise possible to use a formaldehyde source which affords formaldehyde, for instance trioxane or paraformaldehyde. Preferably, the source used for the formaldehyde is an aqueous formaldehyde solution. Preferably, the aqueous formaldehyde solution has a formaldehyde content in the range from 20% to 85% by weight, preferably from 30% to 80% by weight, further preferably from 40% to 60% by weight.

Preferably, stream S1 additionally comprises inert gas.

Preferably, the inert gas content of stream S1 is in the range from 0.1% to 85.0% by volume, preferably in the range from 40% to 75% by volume, further preferably in the range from 50% to 70% by volume, based on the total volume of stream S1.

In the context of the present invention, inert gas shall be all the materials that are gaseous under the process conditions selected in each case and are inert in stage (i). "Inert" in this context means that the gaseous material in a single pass through the reaction zone is converted to an extent of less than 5 mol %, preferably to an extent of less than 2 mol %, more preferably to an extent of less than 1 mol %. Regardless of this definition, water, oxygen, carbon dioxide, carbon monoxide, propionic acid, formic acid, methanol, methyl acetate, acetaldehyde, methyl acrylate, ethene, acetone, methyl formate and acrylic acid shall not be covered by the term "inert gas". In this context, the term "inert gas" as used in the context of the present invention refers either to a single gas or to a mixture of two or more gases. For example, useful inert gases include helium, neon, argon, krypton, radon, xenon, nitrogen, sulfur hexafluoride and gas mixtures of two or more thereof.

Preferably, the inert gas in stream S1 comprises nitrogen. Preferably, at least 95% by weight, further preferably at least 98% by weight, further preferably at least 99% by weight, of the inert gas consists of nitrogen.

In principle, stream S1 is not subject to any particular restrictions with regard to its content of formaldehyde, acetic acid, water, oxygen and inert gas, provided that the ratios in (i) are observed.

Preferably, at least 65% by volume and preferably at least 80% by volume of stream S1 in (i) consists of formaldehyde, acetic acid, water, oxygen and inert gas.

Preferably, stream S1 in (i) additionally comprises one or more of the compounds carbon dioxide, carbon monoxide, and propionic acid, formic acid, methanol, methyl acetate, acetaldehyde, methyl acrylate, ethene, acetone, methyl formate and acrylic acid.

Aldol Condensation Catalyst

The term "aldol condensation catalyst" in the present context is understood to mean any catalyst capable of catalyzing an aldol condensation of the two compounds formaldehyde and acetic acid to give acrylic acid.

In principle, all suitable aldol condensation catalysts are useful in accordance with the invention. Examples, used as unsupported catalysts or in supported form, are alkali metal or alkaline earth metal oxides, mixed oxides comprising vanadium oxide, aluminosilicates or zeolites. Preferably, the aldol condensation catalyst comprises vanadium and optionally phosphorus and optionally oxygen, and also optionally tungsten.

In a preferred configuration, the aldol condensation catalyst comprises vanadium, phosphorus and oxygen, further preferably a vanadium phosphorus oxide.

Further preferably, the aldol condensation catalyst in (ii) comprises a vanadium phosphorus oxide $V_xP_yO_z$ where the x:y weight ratio is preferably in the range from 1:0.5 to 1:5, further preferably from 1:0.7 to 1:4, more preferably from 1:0.8 to 1:3, and the x:z weight ratio is preferably in the range from 1:0.1 to 1:10, further preferably in the range from 1:0.5 to 1:9, more preferably in the range from 1:0.8 to 1:8.

In a further preferred configuration, the aldol condensation catalyst comprises vanadium, phosphorus and oxygen, and additionally tungsten. Further preferably, in this configuration, the aldol condensation catalyst comprises an oxidic composition comprising vanadium, tungsten, phosphorus, oxygen and optionally tin, where the molar ratio of phosphorus to the sum total of vanadium, tungsten and any tin in the oxidic composition is in the range from 1.4:1 to 2.4:1.

The aldol condensation catalyst can be used in the form of an unsupported catalyst or in supported form on one or more substances preferably selected from the group consisting of $SiO_2$, $TiO_2$, $Al_2O_3$ and $ZrO_2$ and mixtures of two or more thereof, further preferably in the form of a supported catalyst.

The aldol condensation catalyst may be present, for example, as granules or extrudates in the form of cylinders, spheres, hollow cylinders, in star form, in tablet form or as a mixture thereof. Preferably, the aldol condensation catalyst is in the form of extrudates, the cross section of the extrudates having a rectangular, triangular, hexagonal, square, polygonal, oval or circular shape. Particular preference is given to using an aldol condensation catalyst in extrudates with a round cross section, the diameter of the round cross-sectional area being in the range from 0.1 to 100 mm, preferably in the range from 0.2 to 80 mm, further preferably in the range from 0.5 to 50 mm, further preferably in the range from 1 to 30 mm, and the length of the extrudates being in the range from 0.1 to 100 mm, preferably in the range from 0.5 to 80 mm, further preferably in the range from 1 to 70 mm.

Contacting of Stream S1 with an Aldol Condensation Catalyst in (ii)

In stage (ii) of the process according to the invention, stream S1 is contacted with an aldol condensation catalyst in a reaction zone to obtain a gaseous stream S2 comprising acrylic acid.

Preferably, the contacting of stream S1 with the aldol condensation catalyst in (ii) is effected continuously.

The contacting in (ii) is preferably effected in at least one reactor, preferably in at least two reactors, further preferably in at least two reactors connected in parallel, which are preferably operated in alternation, the reactors preferably being fixed bed reactors. In the alternating mode of operation, at least one reactor is always in operation. The fixed bed reactors are configured, for example, as shell and tube reactors or thermoplate reactors. In the case of a shell and tube reactor, the catalytically active fixed bed is advantageously within the catalyst tubes, with fluid heat carrier flowing around them.

The catalyst hourly space velocity, the catalyst hourly space velocity being defined as the mass of stream S1 in kg per hour and per unit mass of aldol condensation catalyst in kg, with regard to the contacting in (ii) in the reactor, is preferably chosen such that it is possible to achieve a balanced ratio of the parameters of conversion, selectivity, space-time yield, reactor geometry and reactor dimensions.

Preferably, the contacting in (ii) in a fixed bed reactor is effected at a catalyst hourly space velocity in the range from 0.01 to 50 kg/(h*kg), preferably in the range from 0.1 to 40 kg/(h*kg), further preferably in the range from 0.5 to 30 kg/(h*kg).

The contacting in (ii) in the reactor is not subject to any particular restrictions with regard to the pressure, provided that the contacting of stream S1 with the aldol condensation catalyst gives a stream S2 comprising acrylic acid.

Preferably, the contacting in (ii) in a fixed bed reactor is effected at an absolute pressure in the range from 0.5 to 5 bar, further preferably in the range from 0.8 to 3 bar, further preferably in the range from 1 to 1.8 bar.

Stream S2

The contacting of stream S1 with an aldol condensation catalyst in a reaction zone in (ii) leads to the obtaining of a gaseous stream S2 comprising acrylic acid.

In principle, the stream S2 obtained in (ii) is not subject to any particular restrictions with regard to its temperature.

Preferably, the stream S2 obtained in (ii) is at a temperature in the range from 200 to 450° C., preferably in the range from 250 to 400° C., further preferably in the range from 300 to 400° C.

In principle, it is possible that stream S2 obtained in (ii) comprises at least one further component in addition to acrylic acid. Stream S2 obtained in (ii) especially comprises acrylic acid, formaldehyde and acetic acid.

Preferably, the ratio of the volume of acrylic acid to the sum total of the volumes of formaldehyde and acetic acid in stream S2 obtained in (ii) is in the range from 0.1:1 to 2.0:1, preferably in the range from 0.4:1 to 1.2:1.

As described in detail above, the present invention provides a highly integrated process for preparing acrylic acid, in which the selectivity of acrylic acid formation and/or the yield of acrylic acid can be increased. By running the process in what is called the operating window which is formed by a combination of parameter ranges, it is possible to conduct the process with any desired catalyst.

This illustrates that the process of the invention provides an exceptionally finely adjusted, well-balanced overall process, beginning with the aldol condensation of formaldehyde and acetic acid and ending with the removal of the acrylic acid-comprising product stream, which takes account of all the chemical and energetic specifics of acrylic acid production and configures them advantageously in all aspects.

The present invention is illustrated in detail by the following embodiments and combinations of embodiments which are apparent from the corresponding dependency references and other references:

1. A process for preparing acrylic acid from formaldehyde and acetic acid, comprising
    (i) providing a gaseous stream S1 comprising formaldehyde, acetic acid, oxygen and water, where the formaldehyde content of stream S1 is in the range from 8% to 18% by volume, based on the total volume of stream S1, the ratio of the volumes of acetic acid to formaldehyde is in the range from 0.6:1 to 1.1:1, and the molar ratio of oxygen to the total amount of organic carbon is in the range from 0.02:1 to 0.15:1;
    (ii) contacting stream S1 with an aldol condensation catalyst in a reaction zone to obtain a gaseous stream S2 comprising acrylic acid.

2. The process according to embodiment 1, wherein the ratio of the volumes of formaldehyde to water in stream S1 is in the range from 0.5:1 to 1.5:1, preferably in the range from 0.6:1 to 1.3:1.

3. The process according to embodiment 1 or 2, wherein the space velocity GHSV in the reaction zone is in the range from 800 to 6500 h$^{-1}$ and is defined as the total volume flow rate of stream S1, in m$^3$/h, per unit catalyst volume, in m$^3$, under standard conditions (0° C.; absolute pressure 1.013 bar).

4. The process according to any of embodiments 1 to 3, wherein the temperature in the reaction zone, defined as the temperature at which stream S1 is contacted with the aldol condensation catalyst, is in the range from 350 to 400° C.

5. The process according to any of embodiments 1 to 4, wherein, in stream S1, the ratio of the volumes of formaldehyde to water in stream S1 is in the range from 0.8:1 to 1.3:1.

6. The process according to any of embodiments 1 to 5, wherein the formaldehyde content of stream S1 is in the range from 8% to 14% by volume, based on the total volume of stream S1.

7. The process according to any of embodiments 1 to 6, wherein the ratio of the volumes of acetic acid to formaldehyde in stream S1 is in the range from 0.9:1 to 1.1:1.

8. The process according to any of embodiments 1 to 7, wherein the space velocity GHSV in the reaction zone is in the range from 800 to 2600 h$^{-1}$.

9. The process according to any of embodiments 1 to 8, wherein the temperature in the reaction zone is in the range from 360 to 380° C.

10. The process according to any of embodiments 1 to 4, wherein the formaldehyde content of stream S1 is in the range from 8% to 14% by volume, based on the total volume of stream S1, the ratio of the volumes of acetic acid to formaldehyde in stream S1 is in the range from 0.9:1 to 1.1:1, the molar ratio of oxygen to the total amount of organic carbon is in the range from 0.02:1 to 0.15:1, the ratio of the volumes of formaldehyde to water is in the range from 0.8:1 to 1.3:1, the space velocity GHSV in the reaction zone is in the range from 800 to 2600 h$^{-1}$ and the temperature in the reaction zone is in the range from 360 to 380° C.

11. The process according to any of embodiments 1 to 4, wherein the ratio of the volumes of formaldehyde to water in stream S1 is in the range from 0.8:1 to 1.3:1.

12. The process according to any of embodiments 1 to 4 or 11, wherein the formaldehyde content of stream S1 is in the range from 15% to 18% by volume, based on the total volume of stream S1.

13. The process according to any of embodiments 1 to 4 or 11 to 12, wherein the ratio of the volumes of acetic acid to formaldehyde in stream S1 is in the range from 0.75:1 to 1.1:1.

14. The process according to any of embodiments 1 to 4 or 11 to 13, wherein the space velocity GHSV in the reaction zone is in the range from 800 to 1600 h$^{-1}$.

15. The process according to any of embodiments 1 to 4 or 11 to 14, wherein the temperature in the reaction zone is in the range from 350 to 390° C.

16. The process according to any of embodiments 1 to 4, wherein the formaldehyde content of stream S1 is in the range from 15% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the GHSV in the reaction zone is in the range from 800 to 1600 h$^{-1}$ and the temperature in the reaction zone is in the range from 350 to 390° C.

17. The process according to any of embodiments 1 to 4, wherein the ratio of the volumes of formaldehyde to water in stream S1 is in the range from 0.8:1 to 1.3:1.

18. The process according to any of embodiments 1 to 4 or 17, wherein the ratio of the volumes of acetic acid to formaldehyde in stream S1 is in the range from 0.75:1 to 1.1:1.

19. The process according to any of embodiments 1 to 4 or 17 to 18, wherein the space velocity GHSV in the reaction zone is in the range from 1600 to 6500 h$^{-1}$.

20. The process according to any of embodiments 1 to 4 or 17 to 19, wherein the temperature in the reaction zone is in the range from 380 to 400° C.

21. The process according to any of embodiments 1 to 4, wherein the formaldehyde content of stream S1 is in the range from 8% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the space velocity GHSV in the reaction zone is in the range from 1600 to 6500 h$^{-1}$ and the temperature in the reaction zone is in the range from 380 to 400° C.

22. The process according to any of embodiments 1 to 4, wherein the ratio of the volumes of formaldehyde to water in stream S1 is in the range from 0.6:1 to 1.3:1.

23. The process according to any of embodiments 1 to 4 or 22, wherein the formaldehyde content of stream S1 is in the range from 8% to 14% by volume, based on the total volume of stream S1.

24. The process according to any of embodiments 1 to 4 or 22 to 23, wherein the ratio of the volumes of acetic acid to formaldehyde in stream S1 is in the range from 0.75:1 to 1.1:1.

25. The process according to any of embodiments 1 to 4 or 22 to 24, wherein the space velocity GHSV in the reaction zone is in the range from 800 to 1600 h$^{-1}$.

26. The process according to any of embodiments 1 to 4 or 22 to 25, wherein the temperature in the reaction zone is in the range from 350 to 360° C.

27. The process according to any of embodiments 1 to 4, wherein the formaldehyde content of stream S1 is in the range from 8% to 14% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 1.3:1, the space velocity GHSV in the reaction zone is in the range from 800 to 1600 h$^{-1}$ and the temperature in the reaction zone is in the range from 350 to 360° C.

28. The process according to any of embodiments 1 to 4, wherein the ratio of the volumes of formaldehyde to water in stream S1 is in the range from 0.6:1 to 0.79:1.

29. The process according to any of embodiments 1 to 4 or 28, wherein the formaldehyde content of stream S1 is in the range from 8% to 14% by volume, based on the total volume of stream S1.

30. The process according to any of embodiments 1 to 4 or 28 to 29, wherein the ratio of the volumes of acetic acid to formaldehyde in stream S1 is in the range from 0.66:1 to 1.1:1.

31. The process according to any of embodiments 1 to 4 or 28 to 30, wherein the space velocity GHSV in the reaction zone is in the range from 800 to 1600 h$^{-1}$.

32. The process according to any of embodiments 1 to 4 or 28 to 31, wherein the temperature in the reaction zone is in the range from 360 to 380° C.

33. The process according to any of embodiments 1 to 4, wherein the formaldehyde content of stream S1 is in the range from 8% to 14% by volume, based on the total volume of stream S1, the ratio of the volumes of acetic acid to formaldehyde in stream S1 is in the range from 0.66:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.6:1 to 0.79:1, the GHSV in the reaction zone is in the range from 800 to 1600 h$^{-1}$ and the temperature in the reaction zone is in the range from 360 to 380° C.

34. The process according to any of embodiments 1 to 33, wherein stream S1 additionally comprises inert gas.

35. The process according to embodiment 34, wherein the inert gas content of stream S1 is in the range from 0.1% to 85.0% by volume, preferably in the range from 40% to 75% by volume, further preferably in the range from 50% to 70% by volume, based on the total volume of stream S1.

36. The process according to embodiment 34 or 35, wherein the inert gas in stream S1 comprises nitrogen, and preferably at least 95% by weight, further preferably at least 98% by weight, further preferably at least 99% by weight, of the inert gas consists of nitrogen.

37. The process according to any of embodiments 34 to 36, wherein at least 65% by volume and preferably at least 80% by volume of stream S1 in (i) consists of formaldehyde, acetic acid, water, oxygen and inert gas.

38. The process according to any of embodiments 1 to 37, preferably according to any of embodiments 34 to 37, wherein stream S1 in (i) additionally comprises one or more of the compounds carbon dioxide, carbon monoxide, and propionic acid, formic acid, methanol, methyl acetate, acetaldehyde, methyl acrylate, ethene, acetone, methyl formate and acrylic acid.

39. The process according to any of embodiments 1 to 38, wherein the aldol condensation catalyst in (ii) comprises a vanadium phosphorus oxide $V_xP_yO_z$ where the x:y weight ratio is preferably in the range from 1:0.5 to 1:5, further preferably in the range from 1:0.7 to 1:4, more preferably in the range from 1:0.8 to 1:3, and the x:z weight ratio is preferably in the range from 1:0.1 to 1:10, further preferably in the range from 1:0.5 to 1:9, more preferably in the range from 1:0.8 to 1:8.

40. The process according to any of embodiments 1 to 38, wherein the aldol condensation catalyst in (ii) comprises an oxidic composition comprising vanadium, tungsten, phosphorus, oxygen and optionally tin, where the molar ratio of phosphorus to the sum total of vanadium, tungsten and any tin in the oxidic composition is in the range from 1.4:1 to 2.4:1.

41. The process according to embodiment 39 or 40, wherein the aldol condensation catalyst is used in the form of an unsupported catalyst or in supported form on one or more substances, preferably selected from the group consisting of $SiO_2$, $TiO_2$, $Al_2O_3$ and $ZrO_2$ and mixtures of two or more thereof, preferably in the form of a supported catalyst.

42. The process according to any of embodiments 1 to 42, wherein the contacting in (ii) is effected continuously.

43. The process according to any of embodiments 1 to 42, wherein the contacting in (ii) is effected in at least one reactor, preferably in at least two reactors, further preferably in at least two reactors connected in parallel, which are preferably operated in alternation, the reactors preferably being fixed bed reactors.

44. The process according to embodiment 43, wherein the contacting in (ii) in a fixed bed reactor is effected at a catalyst hourly space velocity in the range from 0.01 to 50 kg/(h*kg), preferably in the range from 0.1 to 40 kg/(h*kg), further preferably in the range from 0.5 to 30 kg/(h*kg), the catalyst hourly space velocity being defined as the mass of stream S1 in kg per hour and per unit mass of aldol condensation catalyst in kg.

45. The process according to embodiment 43 or 44, wherein the contacting in (ii) in a fixed bed reactor is effected at an absolute pressure in the range from 0.5 to 5 bar, further preferably in the range from 0.8:1 to 3 bar, further preferably in the range from 1 to 1.8 bar.

46. The process according to any of embodiments 1 to 45, wherein stream S2 obtained in (ii) is at a temperature in the range from 200 to 450° C., preferably in the range from 250 to 400° C., further preferably in the range from 300 to 400° C.

47. The process according to any of embodiments 1 to 46, wherein the ratio of the volume of acrylic acid to the sum total of the volumes of formaldehyde and acetic acid in stream S2 obtained in (ii) is in the range from 0.1:1 to 2.0:1, preferably in the range from 0.4:1 to 1.2:1.

U.S. Provisional Patent Application No. 62/253,702, filed Nov. 11, 2015, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

DESCRIPTION OF THE FIGURES

FIG. 1 shows the selectivity of acrylic acid formation in % (ordinate, 50% to 100%) versus the carbon conversion (C) in % (abscissa, 20% to 80%) for inventive operating windows according to table 7.

The present invention is illustrated further by the examples which follow.

EXAMPLES

I. Analysis
1.1 Gas Chromatography
For analysis of the product stream, an online Agilent 7890A GCMS system was used.
Sampling was effected by a 10-port valve having a 500 μL sample loop or 1000 μL sample loop.
The analysis parameters can be expressed as follows:
MS/FID:
FFAP 25 m×0.32 mm×0.5 μm, carrier gas He, split 5:1, column flow rate 15 mL/min
TCD:
DB624 3 m×0.25 mm×1.4 μm
Volamine 60 m×0.32 mm, carrier gas He, split 5:1, column flow rate 15 mL/min
TCD2:
RTX5 30 m×0.32 mm×1.0 μm
Select permanent gases/CO2 HR carrier gas He, split 2:1, column flow rate: 30 mL/min
The temperature program was selected as follows:
hold at 40° C. for 2.5 min
heat to 105° C. at a heating rate of 20 K/min
heat to 225° C. at a heating rate of 40 K/min
hold at 225° C. for 2.75 min II. Chemicals

| Chemical | Supplier | Purity |
|---|---|---|
| vanadium(V) oxide | Sigma Aldrich | >99.6% |
| oxalic acid dihydrate | Acros Organics | >99% |
| phosphoric acid | Acros Organics | >85% |
| ammonium metatungstate | Sigma Aldrich | >99% |
| tin(II) oxalate | Merck | >98% |
| potassium nitrate | Merck | >99% |
| lanthanum(III) nitrate hexahydrate | Sigma Aldrich | >99% |

III. Preparation of Catalysts 1 to 4 and 6 to 19
III.1 Preparation of Highly Concentrated Solutions of $V_2O_5$ in Aqueous Oxalic Acid
1.1 Molar Solution of $V_2O_5$ in Oxalic Acid
A 2 L three-neck flask was initially charged with 800 mL of aqueous oxalic acid dihydrate solution. While stirring, 1.1 mol of $V_2O_5$ were added to this solution and heated to 80° C. by means of a heating bath and refluxed. Oxalic acid dihydrate in solid form was then added in portions to the orange-brown suspension and the flask was sealed again. Evolution of gas and foam was observed here (redox reaction between $V_2O_5$ and oxalic acid). The addition of oxalic acid dihydrate was then repeated until the original suspension had become a deep blue solution. For this purpose, about three times the molar amount of oxalic acid dihydrate was needed (based on the molar amount of $V_2O_5$). The vanadium was then present in the form of a solution of vanadyl oxalate $VO(C_2O_4)$ with a molar concentration of vanadium of 2.2 mol/L. The solution thus obtained was cooled down to room temperature and transferred quantitatively into a 1 L standard flask (rinsing in with demineralized water, DM water). DM water was used to make it up to 1 liter.

The mass of vanadium pentoxide to be weighed in (Sigma Aldrich Prod. Nr.: 221899) was determined by the following formula:

$$m(V2O5) = \frac{2 \cdot M(V) \cdot c \cdot V}{wt\ \%}$$

M(V)=molar mass of V
c=concentration of the solution to be prepared
V=batch volume
% by wt.=vanadium content of the $V_2O_5$ (manufacturer's certificate of analysis)

$$m(V2O5) = \frac{2 \cdot 50.94\ g/mol \cdot 1.1\ mol/L \cdot 1\ L}{0.562} = 199.41\ g$$

III.2 General Details

The ignition loss (LOI hereinafter) of the support was determined beforehand. In this way, the exact content of oxidic components was known and it was possible to correct the starting support weight with this value. It was thus possible to ensure that the desired loading with active components was attained. The LOI of the Q20C support (CARiACT Q20C silica from Fuji Silysia) was 2.95%.

The impregnations were conducted to 100% of the water uptake (hereinafter 100% ICW) with mixed solutions of DM water and active component.

The loadings in the case of supported catalysts were given in "% by weight on support". This means that, for example, for a "9.36V/11.3 P/Q20C" catalyst, for the loading with vanadium, 9.36% by weight of the mass of support used had to be loaded onto the support as vanadium.

III.3 Synthesis 31.18 g of the Q20C support were weighed into a porcelain dish (base diameter 18 cm) and placed onto an agitator. The latter was set such that the sample was kept in motion. By means of a 3 mL disposable pipette, the vanadium impregnation solution was then applied dropwise uniformly to the support and homogenized with a spatula. The mixture then remained on the agitator for 30 minutes and was subsequently dried in an air circulation drying cabinet at 80° C. As soon as the sample was dry, it was cooled back down to room temperature.

Lastly, the sample was impregnated with the phosphorus impregnation solution (identical procedure) and likewise dried.

For the further elements, tungsten and optionally tin, it was to be noted that vanadium was preferably always impregnated as the first element and phosphorus as the last. Thus, if further elements were applied in addition to vanadium and phosphorus, vanadium was preferably always impregnated as the first element and then dried. Gradually, all the further elements were then applied by this procedure. As the final impregnation, phosphorus was always applied as phosphoric acid solution.

It was also possible to conduct co-impregnations. For this purpose, impregnation solutions with several components were prepared and impregnated for the corresponding step.

After the final drying, the samples were calcined. For this purpose, they were heated to 260° C. in a muffle furnace (M110 from Heraeus) in an air stream (1 L/min) with a heating ramp of 1 K/min and kept at 260° C. for two hours and then cooled down to room temperature. The samples were taken out of the muffle furnace and fine fractions formed (<315 μm) were removed by manual sieving.

Typically, all the components were used as aqueous solutions of the nitrates. An exception to this was tin(II) oxalate, since it only had good solubility (1 mol/L) in semiconcentrated nitric acid. Tungsten was used in the form of ammonium metatungstate in aqueous solution.

Calculation Example
Starting support weight, LOI corrected 31.18 g−31.18 g*0.0295=30.260 g Water uptake of the support (100% ICW)

31.18 g*1.04 mL/g=32.427 mL~32.43 mL

Calculation of the mass of vanadium $$m_{(V)}=(m_{(support)}-m_{(support)}*LOI)*\%\ by\ wt.\ on\ support_{(v)}$$

$$m_{(V)}=(31.18\ g-31.18\ g*0.0295)*0.0936=2.832\ g$$

Calculation of the volume of $VO(C_2O_4)$ solution $$m_{(V)}=M_{(V)}*c_{(V)}*V_{(V)} \rightarrow V_{(V)}=m_{(V)}/(M_{(V)}*c_{(V)})$$

$$V_{(V)}=2.832\ g/(50.94\ g/mol*2.2\ mol/L)=25.27\ mL$$

Calculation of the mass of phosphorus $$m_{(P)}=(m_{(support)}-m_{(support)}*LOI)*\%\ by\ wt.\ on\ support_{(P)}$$

$$m_{(P)}=(31.18\ g-31.18\ g*0.0295)*0.113=3.419\ g$$

Calculation of the volume of $H_3PO_4$ solution $$m_{(P)}=M_{(P)}*c_{(P)}*V_{(P)} \rightarrow V_{(P)}=m_{(P)}/M_{(P)}*c_{(P)})$$

$$V_{(P)}=3.419\ g/(30.97\ g/mol*6\ mol/L)=18.40\ mL$$

Making up the impregnation solutions for 100% ICW
Vanadium impregnation solution V(H2O content)=31.18 g*1.04 g/mL−$V_{(P)}$=35.43 mL−25.27 mL=10.16 mL Phosphorus Impregnation Solution V(H2O content)=31.18 g*1.04 g/mL−$V_{(P)}$=35.43 mL−18.40 mL=17.03 mL IV Preparation of Catalyst 5

Oxidic Catalyst Comprising Vanadium, Tungsten, Phosphorus and Bismuth on Silica Support 167.5 g of ammonium metavanadate were added to 3 liters of a 20% by weight aqueous solution of citric acid. The mixture was heated to 50° C. and stirred until dissolution was complete. 116 g of a colloidal silica suspension (Ludox AS 40) were added, followed by 227.8 g of ethylene glycol. The mixture was heated to 80° C. and stirred for 30 minutes. 35.3 g of ammonium metatungstate were dissolved in 500 mL of deionized water and added dropwise to the mixture. The mixture was then stirred at 80° C. for 15 minutes. 347.2 g of bismuth nitrate hexahydrate were dissolved in 480 mL of a 10% nitric acid solution. The acidic bismuth solution was added dropwise to the previous mixture and stirred at 80° C. for 30 minutes, then cooled down to 30° C. while stirring constantly. 1232 mL of a 2% solution of methyl cellulose were added and then the mixture was stirred for a further 30 minutes. Finally, 303.7 g of an 85% phosphoric acid solution were added and the mixture was stirred for 30 minutes. The resulting mixture was dried at 80° C. in a drying oven for 48 h.

For safety reasons, the resulting solid material was calcined in an atmosphere having 3% by volume of $O_2$/97% by volume of N2 in accordance with the following temperature profile:
i) heating from room temperature to 160° C. at a rate of 10° C. per minute;
ii) heating at 160° C. for 2 hours;
iii) heating from 160° C. to 250° C. at a rate of 3° C. per minute;
iv) heating at 250° C. for 2 hours;
v) heating from 250° C. to 300° C. at a rate of 3° C. per minute;
vi) heating at 300° C. for 6 hours;
vii) heating from 300° C. to 450° C. at a rate of 3° C. per minute;
viii) heating at 450° C. for 6 hours.

VI Catalyst Compositions

Compositions of catalysts which have been prepared according to IV and V are specified in table 1 with % by weight figures for phosphorus (P), vanadium (V) and any tungsten (W), any potassium (K) and any lanthanum (La), and any support material.

VIII Parameter Ranges

The parameters specified in VII were examined for selected ranges; the combination of the respective ranges for the six parameters is referred to as "operating window" (W). The five operating windows in total are shown in tables 2 to 6 below.

TABLE 2

| Operating window 1 (W1) | | |
| --- | --- | --- |
| | from | to |
| GHSV | 800 | 2600 |
| Temperature | 360 | 380 |
| FA | 8 | 14 |
| ACE/FA | 0.9 | 1.1 |
| FA/H2O | 0.8 | 1.2 |
| O2/TOC | 0.02 | 0.15 |

TABLE 1

Overview of catalysts comprising phosphorus (P), vanadium (V) and optionally further elements (W, K, La) which have been used for catalytic studies

| No. | Catalyst | Vanadium content [% by wt.] | Phosphorus content [% by wt.] | Tungsten content [% by wt.] | Further element [% by wt.] | See table |
| --- | --- | --- | --- | --- | --- | --- |
| 1 | 9.36V/11.3P@Q20C | 9.36 | 11.3 | — | — | 7 |
| 2 | 11.15W + 8.43V/12.42P@Q20C | 8.43 | 12.42 | 11.15 | | 8 |
| 3 | 11.61W + 7.5V/12.42P@Q20C | 7.5 | 12.42 | 11.61 | | 9 |
| 4 | 7.5V + 8.93W + 0.576K + 11.53P @Q20C | 7.5 | 11.53 | 8.93 | K, 0.576 | 10 |
| 5 | 11.4V + 3.8W + 7Bi + 12.7P (unsupported catalyst) | 11.4 | 12.7 | 3.8 | Bi, 7 | 11 |
| 6 | 7.5V + 8.93W + 2.045La + 11.53P @Q20C | 7.5 | 11.53 | 8.93 | La, 2.045 | 12 |
| 7 | 8.12W + 7.5V/11.3P@Q20C | 7.5 | 11.3 | 8.12 | | 13 |
| 8 | 8.93W + 7.5V/11.3P@Q20C | 7.5 | 11.3 | 8.93 | | 14 |
| 9 | 9.74W + 7.5V/11.3P@Q20C | 7.5 | 11.3 | 9.74 | | 15 |
| 10 | 11.61W + 7.5V/11.3P@Q20C | 7.5 | 11.3 | 9.74 | | 16 |
| 11 | 8.93W + 7.5V/11.53P@Q20C | 7.5 | 11.53 | 8.93 | | 17 |
| 12 | 11.61W + 7.5V/12.42P@Q20C | 7.5 | 12.42 | 11.61 | | 18 |
| 13 | 11.15W + 8.43V/12.42P@Q20C | 8.43 | 12.42 | 11.15 | | 19 |

@Q20C: supported on Q20C

VII Parameters

The following parameters were considered:

GHSV [$h^{-1}$]  total volume flow rate of stream S1, in $m^3$/h, per unit catalyst volume, in $m^3$, under standard conditions (0° C. and absolute pressure 1.013 bar);
Temperature  temperature at which stream S1 has been contacted with the aldol condensation catalyst in ° C.;
FA  formaldehyde content of stream S1 in % by volume, based on the total volume of stream S1;
ACE/FA  ratio of the volumes of acetic acid to formaldehyde in stream S1;
FA/$H_2$O  ratio of the volumes of formaldehyde to water in stream S1;
$O_2$/TOC  molar ratio of oxygen to the total amount of organic carbon in stream S1.

TABLE 3

| Operating window 2 (W2) | | |
| --- | --- | --- |
| | from | to |
| GHSV | 800 | 1600 |
| Temperature | 350 | 390 |
| FA | 15 | 18 |
| ACE/FA | 0.75 | 1.1 |
| FA/H2O | 0.8 | 1.2 |
| O2/TOC | 0.02 | 0.15 |

TABLE 4

| Operating window 3 (W3) | | |
| --- | --- | --- |
| | from | to |
| GHSV | 1600 | 6500 |
| Temperature | 380 | 400 |

TABLE 4-continued

Operating window 3 (W3)

|  | from | to |
|---|---|---|
| FA | 8 | 18 |
| ACE/FA | 0.75 | 1.1 |
| FA/H2O | 0.8 | 1.2 |
| O2/TOC | 0.02 | 0.15 |

TABLE 5

Operating window 4 (W4)

|  | from | to |
|---|---|---|
| GHSV | 800 | 1600 |
| Temperature | 350 | 360 |
| FA | 8 | 14 |
| ACE/FA | 0.75 | 1.1 |
| FA/H2O | 0.6 | 1.2 |
| O2/TOC | 0.02 | 0.15 |

TABLE 6

Operating windows 5 (W5)

|  | from | to |
|---|---|---|
| GHSV | 800 | 1600 |
| Temperature | 360 | 380 |
| FA | 8 | 14 |
| ACE/FA | 0.66 | 1.1 |
| FA/H2O | 0.6 | 0.79 |
| O2/TOC | 0.02 | 0.15 |

IX Catalytic Studies/Use of the Catalysts in the Preparation of Acrylic Acid

The catalytic studies were conducted on pulverulent samples, for which a spall fraction having a particle size in the range from 0.315 to 0.5 mm was used. For preparation for the studies, the samples were positioned in tubular reactors between two inert particle beds consisting of quartz glass spall, the laden reactors were installed into the catalysis apparatus, a 16-tube high-throughput screening system, and the samples present therein were subjected to the test protocols.

For this purpose, a stream consisting of formaldehyde, acetic acid, water and argon was heated to 175° C. and hence evaporated. The gaseous mixture was then contacted with an aldol condensation catalyst in pulverulent form at 1.1 bar [temperature and GHSV as specified in tables 7 to 19]. The temperature was measured at the start of the experimentation by means of a thermocouple in the isothermal zone of the reactor, i.e. of the catalyst bed, and corresponded to the temperature at which the reactions were conducted. The product stream was subsequently diluted with nitrogen, and the composition was determined by gas chromatography.

Tables 7 to 19 illustrate the invention. Catalytic results in inventive operating windows (F) and outside them (CE) were compared for different catalysts according to III and IV in terms of carbon conversion (C) and selectivity of acrylic acid formation [S (ACR)].

The carbon conversion (C) was calculated by the following equation:

$$C = 100 * (NC^P_{sum}/(NC^E_{FA} + NC^E_{ACE}))$$

$$NC^P_{sum} = (NC^E_{FA} + NC^E_{ACE}) - (NC^P_{FA} + NC^P_{ACE});$$

$NC^E_{FA}$=number of carbon atoms present in the stream in the form of a formaldehyde source $NC^E_{ACE}$=number of carbon atoms present in the stream in the form of acetic acid $NC^P_{FA}$=number of carbon atoms present in the product stream in the form of a formaldehyde source $NC^P_{ACE}$=number of carbon atoms present in the product stream in the form of acetic acid.

The acrylic acid selectivity (S) was calculated by the following formula:

$$S = 100(NC^P_{AS}/NC^P_{sum}).$$

A negative effect was considered to be a drop in acrylic acid selectivity [S(ACR)] and/or a drop in carbon conversion (C). A positive effect was considered to be an increase in acrylic acid selectivity (S(ACR)) and/or an increase in carbon conversion (C).

TABLE 7

Catalyst 1 (9.36V/11.3P/Q20C)

| Operating window | Gas O2 [%] | O2/TOC | Gas H2O [%] | ACE/FA | Gas ACE [%] | GHSV [h-1] | Gas FA [%] | Temperature [° C.] | FA/H2O | Carbon conversion (C) [%] | S(ACR) [%] |
|---|---|---|---|---|---|---|---|---|---|---|---|
| W1 | 1.944 | 0.072 | 9 | 1 | 9 | 995 | 9 | 360 | 1 | 67.5 | 81.9 |
| W1 | 2.592 | 0.072 | 15 | 1 | 12 | 995 | 12 | 360 | 0.8 | 63 | 82.1 |
| W1 | 2.592 | 0.072 | 12 | 1 | 12 | 995 | 12 | 380 | 1 | 66 | 75.6 |
| W1 | 2.592 | 0.072 | 15 | 1 | 12 | 995 | 12 | 360 | 0.8 | 72.5 | 68.6 |
| W1 | 2.16 | 0.072 | 10 | 1 | 10 | 796 | 10 | 360 | 1 | 64.3 | 76.6 |
| W1 | 1.944 | 0.072 | 11.3 | 1 | 9 | 995 | 9 | 380 | 0.8 | 66.4 | 72.8 |
| W1 | 1.433 | 0.053 | 9 | 1 | 9 | 995 | 9 | 360 | 1 | 59.7 | 80.3 |
| W1 | 2.592 | 0.072 | 15 | 1 | 12 | 995 | 12 | 360 | 0.8 | 60.4 | 78.5 |
| W1 | 1.2 | 0.04 | 8.3 | 1 | 10 | 796 | 10 | 360 | 1.2 | 59.7 | 75.8 |
| W1 | 1.2 | 0.04 | 10 | 1 | 10 | 796 | 10 | 360 | 1 | 55.3 | 77 |
| W4 | 1.944 | 0.072 | 9 | 1 | 9 | 995 | 9 | 350 | 1 | 62.1 | 82.3 |
| W4 | 0.96 | 0.04 | 8 | 1 | 8 | 796 | 8 | 355 | 1 | 59 | 78.6 |
| W3 | 3.24 | 0.072 | 18.8 | 1 | 15 | 3617 | 15 | 380 | 0.8 | 63.9 | 75.4 |
| CE | 2.592 | 0.072 | 12 | 1 | 12 | 995 | 12 | 340 | 1 | 52.4 | 85.6 |
| CE | 1.944 | 0.072 | 9 | 1 | 9 | 3617 | 9 | 360 | 1 | 50.8 | 85.6 |
| CE | 1.944 | 0.072 | 9 | 1 | 9 | 3617 | 9 | 350 | 1 | 51.8 | 79.6 |
| CE | 1.944 | 0.072 | 9 | 1 | 9 | 2894 | 9 | 350 | 1 | 52.6 | 78.2 |
| CE | 0.96 | 0.04 | 8 | 1 | 8 | 2894 | 8 | 355 | 1 | 48.8 | 83.2 |
| CE | 1.433 | 0.053 | 9 | 1 | 9 | 3617 | 9 | 360 | 1 | 49.1 | 81.4 |
| CE | 2.592 | 0.072 | 15 | 1 | 12 | 3617 | 12 | 360 | 0.8 | 48.3 | 82.1 |
| CE | 1.38 | 0.051 | 15.2 | 1 | 9 | 4543 | 9 | 370 | 0.6 | 48.5 | 80 |

TABLE 7-continued

Catalyst 1 (9.36V/11.3P/Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 1.38 | 0.051 | 15.2 | 1 | 9 | 4543 | 9 | 370 | 0.6 | 48.9 | 79.4 |
| CE | 1.38 | 0.051 | 15.2 | 1 | 9 | 4543 | 9 | 370 | 0.6 | 49 | 79.1 |
| CE | 1.38 | 0.051 | 15.2 | 1 | 9 | 4543 | 9 | 370 | 0.6 | 48.1 | 80 |
| CE | 3.24 | 0.072 | 18.8 | 1 | 15 | 995 | 15 | 340 | 0.8 | 45.8 | 83.5 |
| CE | 3.24 | 0.072 | 15 | 1 | 15 | 3617 | 15 | 360 | 1 | 43.8 | 85.6 |
| CE | 2.592 | 0.072 | 20.3 | 1 | 12 | 3617 | 12 | 340 | 0.6 | 49.2 | 75.8 |
| CE | 1.944 | 0.072 | 11.3 | 1 | 9 | 3617 | 9 | 340 | 0.8 | 45.9 | 81.1 |
| CE | 2.592 | 0.072 | 15 | 1 | 12 | 3617 | 12 | 360 | 0.8 | 43.8 | 84.9 |
| CE | 1.38 | 0.051 | 15.2 | 1 | 9 | 4543 | 9 | 370 | 0.6 | 46.3 | 79.6 |
| CE |  | 0 | 15.2 | 1 | 9 |  | 9 | 370 | 0.6 | 46.3 | 79.6 |
| CE | 1.08 | 0.04 | 15.2 | 1 | 9 | 3617 | 9 | 350 | 0.6 | 44.4 | 81.7 |
| CE | 0.922 | 0.034 | 9 | 1 | 9 | 3617 | 9 | 360 | 1 | 40.7 | 82 |
| CE | 3.24 | 0.072 | 25.3 | 1 | 15 | 3617 | 15 | 360 | 0.6 | 39.9 | 75.9 |
| CE | 2.592 | 0.072 | 12 | 1 | 12 | 3617 | 12 | 340 | 1 | 31 | 88.2 |
| CE | 3.24 | 0.072 | 18.8 | 1 | 15 | 3617 | 15 | 340 | 0.8 | 26.4 | 84.8 |
| CE | 1.2 | 0.04 | 10 | 1 | 10 | 2894 | 10 | 360 | 1 | 46.7 | 82.8 |
| CE | 0.96 | 0.04 | 6.7 | 1 | 8 | 2894 | 8 | 360 | 1.2 | 46.7 | 78.8 |

For the operating windows of the invention, a positive effect on the carbon conversion (C) was found with comparably good selectivity of acrylic acid formation. The results from table 7 are shown in the form of a graph in FIG. 1.

TABLE 8

Catalyst 2 (11.15W + 8.43V/12.42P@Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W1 | 1.2 | 0.04 | 8.3 | 1 | 10 | 816 | 10 | 360 | 1.2 | 62.7 | 79.2 |
| W1 | 1.944 | 0.072 | 9 | 1 | 9 | 1020 | 9 | 360 | 1 | 69.3 | 83.6 |
| W1 | 2.16 | 0.072 | 10 | 1 | 10 | 816 | 10 | 360 | 1 | 68 | 79.2 |
| W1 | 1.433 | 0.053 | 9 | 1 | 9 | 1020 | 9 | 360 | 1 | 63.2 | 82.2 |
| W1 | 2.592 | 0.072 | 12 | 1 | 12 | 1020 | 12 | 380 | 1 | 66.2 | 77.6 |
| W4 | 1.944 | 0.072 | 9 | 1 | 9 | 1020 | 9 | 350 | 1 | 66.4 | 83.6 |
| W4 | 0.96 | 0.04 | 8 | 1 | 8 | 816 | 8 | 355 | 1 | 61.7 | 81.2 |
| W1 | 2.592 | 0.072 | 15 | 1 | 12 | 1020 | 12 | 360 | 0.8 | 65.8 | 83 |
| W1 | 2.592 | 0.072 | 15 | 1 | 12 | 1020 | 12 | 360 | 0.8 | 73.5 | 70.4 |
| W1 | 2.592 | 0.072 | 15 | 1 | 12 | 1020 | 12 | 360 | 0.8 | 64.3 | 80.3 |
| W1 | 1.944 | 0.072 | 11.3 | 1 | 9 | 1020 | 9 | 380 | 0.8 | 67.5 | 75.2 |
| W3 | 3.24 | 0.072 | 18.8 | 1 | 15 | 3789 | 15 | 380 | 0.8 | 66 | 78.3 |
| CE | 2.592 | 0.072 | 20.3 | 1 | 12 | 3789 | 12 | 380 | 0.6 | 59.7 | 78.9 |
| CE | 2.16 | 0.08 | 15.2 | 1 | 9 | 3032 | 9 | 360 | 0.6 | 58.8 | 77.4 |
| CE | 1.944 | 0.072 | 15.2 | 1 | 9 | 3789 | 9 | 360 | 0.6 | 50.1 | 80.8 |
| CE | 3.24 | 0.072 | 25.3 | 1 | 15 | 1020 | 15 | 360 | 0.6 | 61.5 | 80.4 |
| CE | 1.38 | 0.051 | 15.2 | 1 | 9 | 4759 | 9 | 370 | 0.6 | 52.5 | 82 |
| CE | 1.38 | 0.051 | 15.2 | 1 | 9 | 4759 | 9 | 370 | 0.6 | 52.5 | 81.4 |
| CE | 1.38 | 0.051 | 15.2 | 1 | 9 | 4759 | 9 | 370 | 0.6 | 52 | 82 |
| CE | 1.38 | 0.051 | 15.2 | 1 | 9 | 4759 | 9 | 370 | 0.6 | 52.4 | 81.1 |
| CE | 1.38 | 0.051 | 15.2 | 1 | 9 | 4759 | 9 | 370 | 0.6 | 49.6 | 81.5 |
| CE |  | 0 | 15.2 | 1 | 9 |  | 9 | 370 | 0.6 | 49.6 | 81.5 |
| CE | 1.2 | 0.04 | 10 | 1 | 10 | 3032 | 10 | 360 | 1 | 52.1 | 86.3 |
| CE | 0.96 | 0.04 | 6.7 | 1 | 8 | 3032 | 8 | 360 | 1.2 | 52.8 | 83.3 |
| CE | 2.592 | 0.072 | 20.3 | 1 | 12 | 3789 | 12 | 340 | 0.6 | 51.5 | 78.3 |
| CE | 1.08 | 0.04 | 15.2 | 1 | 9 | 3789 | 9 | 350 | 0.6 | 45 | 82.8 |
| CE | 1.944 | 0.072 | 11.3 | 1 | 9 | 1020 | 9 | 340 | 0.8 | 62.5 | 78.8 |
| CE | 0.96 | 0.04 | 8 | 1 | 8 | 3032 | 8 | 355 | 1 | 53.8 | 86.7 |
| CE | 1.944 | 0.072 | 9 | 1 | 9 | 3789 | 9 | 350 | 1 | 54.2 | 83.7 |
| CE | 1.944 | 0.072 | 9 | 1 | 9 | 3789 | 9 | 360 | 1 | 51.6 | 87.6 |
| CE | 1.944 | 0.072 | 9 | 1 | 9 | 3032 | 9 | 350 | 1 | 54.9 | 82.2 |
| CE | 1.433 | 0.053 | 9 | 1 | 9 | 3789 | 9 | 360 | 1 | 52.8 | 84.9 |
| CE | 3.24 | 0.072 | 25.3 | 1 | 15 | 3789 | 15 | 360 | 0.6 | 41.9 | 78.2 |
| CE | 2.592 | 0.072 | 20.3 | 1 | 12 | 1007 | 12 | 340 | 0.6 | 64.9 | 79.8 |
| CE | 3.24 | 0.072 | 18.8 | 1 | 15 | 1020 | 15 | 340 | 0.8 | 50.4 | 84.8 |
| CE | 3.24 | 0.072 | 25.3 | 1 | 15 | 1007 | 15 | 360 | 0.6 | 57 | 82.8 |
| CE | 2.592 | 0.072 | 12 | 1 | 12 | 1020 | 12 | 340 | 1 | 49 | 86.7 |
| CE | 1.38 | 0.051 | 15.2 | 1 | 9 | 4543 | 9 | 370 | 0.6 | 46.5 | 83.3 |
| CE | 2.592 | 0.072 | 15 | 1 | 12 | 3789 | 12 | 360 | 0.8 | 50.3 | 83.7 |

TABLE 8-continued

Catalyst 2 (11.15W + 8.43V/12.42P@Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 2.592 | 0.072 | 15 | 1 | 12 | 3789 | 12 | 360 | 0.8 | 47.1 | 86.8 |
| CE | 3.24 | 0.072 | 15 | 1 | 15 | 3789 | 15 | 360 | 1 | 46.3 | 87.8 |
| CE | 2.592 | 0.072 | 20.3 | 1 | 12 | 3617 | 12 | 340 | 0.6 | 48.5 | 79.8 |
| CE | 1.38 | 0.051 | 15.2 | 1 | 9 | 4543 | 9 | 370 | 0.6 | 46.3 | 83.1 |
| CE | 1.38 | 0.051 | 15.2 | 1 | 9 | 4543 | 9 | 370 | 0.6 | 46.2 | 83 |
| CE | 1.944 | 0.072 | 11.3 | 1 | 9 | 3789 | 9 | 340 | 0.8 | 48.4 | 83.2 |
| CE | 0.922 | 0.034 | 9 | 1 | 9 | 3789 | 9 | 360 | 1 | 46.4 | 85.8 |
| CE | 1.38 | 0.051 | 15.2 | 1 | 9 | 4543 | 9 | 370 | 0.6 | 45 | 83.1 |
| CE | 1.38 | 0.051 | 15.2 | 1 | 9 | 4543 | 9 | 370 | 0.6 | 44 | 82.2 |
| CE | 2.592 | 0.072 | 12 | 1 | 12 | 3789 | 12 | 340 | 1 | 32 | 90 |
| CE | 3.24 | 0.072 | 18.8 | 1 | 15 | 3789 | 15 | 340 | 0.8 | 29.2 | 87.1 |

For the inventive operating windows, a positive effect on the carbon conversion (C) was found with comparably good selectivity of acrylic acid formation.

TABLE 9

Catalyst 3 (11.61W + 7.5V/12.42P@Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W1 | 1.2 | 0.04 | 8.3 | 1 | 10 | 816 | 10 | 360 | 1.2 | 62.7 | 79.2 |
| W1 | 1.944 | 0.072 | 9 | 1 | 9 | 1020 | 9 | 360 | 1 | 69.3 | 83.6 |
| W1 | 2.16 | 0.072 | 10 | 1 | 10 | 816 | 10 | 360 | 1 | 68 | 79.2 |
| W1 | 1.433 | 0.053 | 9 | 1 | 9 | 1020 | 9 | 360 | 1 | 63.2 | 82.2 |
| W1 | 2.592 | 0.072 | 12 | 1 | 12 | 1020 | 12 | 380 | 1 | 66.2 | 77.6 |
| W4 | 1.944 | 0.072 | 9 | 1 | 9 | 1020 | 9 | 350 | 1 | 66.4 | 83.6 |
| W4 | 0.96 | 0.04 | 8 | 1 | 8 | 816 | 8 | 355 | 1 | 61.7 | 81.2 |
| W1 | 2.592 | 0.072 | 15 | 1 | 12 | 1020 | 12 | 360 | 0.8 | 65.8 | 83 |
| W1 | 2.592 | 0.072 | 15 | 1 | 12 | 1020 | 12 | 360 | 0.8 | 73.5 | 70.4 |
| W1 | 2.592 | 0.072 | 15 | 1 | 12 | 1020 | 12 | 360 | 0.8 | 64.3 | 80.3 |
| W1 | 1.944 | 0.072 | 11.3 | 1 | 9 | 1020 | 9 | 380 | 0.8 | 67.5 | 75.2 |
| W3 | 3.24 | 0.072 | 18.8 | 1 | 15 | 3789 | 15 | 380 | 0.8 | 66 | 78.3 |
| CE | 2.592 | 0.072 | 20.3 | 1 | 12 | 3789 | 12 | 380 | 0.6 | 59.7 | 78.9 |
| CE | 2.16 | 0.08 | 15.2 | 1 | 9 | 3032 | 9 | 360 | 0.6 | 58.8 | 77.4 |
| CE | 1.944 | 0.072 | 15.2 | 1 | 9 | 3789 | 9 | 360 | 0.6 | 50.1 | 80.8 |
| CE | 3.24 | 0.072 | 25.3 | 1 | 15 | 1020 | 15 | 360 | 0.6 | 61.5 | 80.4 |
| CE | 1.38 | 0.051 | 15.2 | 1 | 9 | 4759 | 9 | 370 | 0.6 | 52.5 | 82 |
| CE | 1.38 | 0.051 | 15.2 | 1 | 9 | 4759 | 9 | 370 | 0.6 | 52.5 | 81.4 |
| CE | 1.38 | 0.051 | 15.2 | 1 | 9 | 4759 | 9 | 370 | 0.6 | 52 | 82 |
| CE | 1.38 | 0.051 | 15.2 | 1 | 9 | 4759 | 9 | 370 | 0.6 | 52.4 | 81.1 |
| CE | 1.38 | 0.051 | 15.2 | 1 | 9 | 4759 | 9 | 370 | 0.6 | 49.6 | 81.5 |
| CE | | 0 | 15.2 | 1 | 9 | | 9 | 370 | 0.6 | 49.6 | 81.5 |
| CE | 1.2 | 0.04 | 10 | 1 | 10 | 3032 | 10 | 360 | 1 | 52.1 | 86.3 |
| CE | 0.96 | 0.04 | 6.7 | 1 | 8 | 3032 | 8 | 360 | 1.2 | 52.8 | 83.3 |
| CE | 2.592 | 0.072 | 20.3 | 1 | 12 | 3789 | 12 | 340 | 0.6 | 51.5 | 78.3 |
| CE | 1.08 | 0.04 | 15.2 | 1 | 9 | 3789 | 9 | 350 | 0.6 | 45 | 82.8 |
| CE | 1.944 | 0.072 | 11.3 | 1 | 9 | 3789 | 9 | 380 | 0.8 | 60.3 | 81.9 |
| CE | 1.944 | 0.072 | 11.3 | 1 | 9 | 1020 | 9 | 340 | 0.8 | 62.5 | 78.8 |
| CE | 2.592 | 0.072 | 12 | 1 | 12 | 3789 | 12 | 380 | 1 | 58 | 82.9 |
| CE | 0.96 | 0.04 | 8 | 1 | 8 | 3032 | 8 | 355 | 1 | 53.8 | 86.7 |
| CE | 1.944 | 0.072 | 9 | 1 | 9 | 3789 | 9 | 350 | 1 | 54.2 | 83.7 |
| CE | 1.944 | 0.072 | 9 | 1 | 9 | 3789 | 9 | 360 | 1 | 51.6 | 87.6 |
| CE | 1.944 | 0.072 | 9 | 1 | 9 | 3032 | 9 | 350 | 1 | 54.9 | 82.2 |
| CE | 1.433 | 0.053 | 9 | 1 | 9 | 3789 | 9 | 360 | 1 | 52.8 | 84.9 |
| CE | 3.24 | 0.072 | 25.3 | 1 | 15 | 3789 | 15 | 360 | 0.6 | 41.9 | 78.2 |
| CE | 2.592 | 0.072 | 20.3 | 1 | 12 | 1007 | 12 | 340 | 0.6 | 64.9 | 79.8 |
| CE | 3.24 | 0.072 | 18.8 | 1 | 15 | 1020 | 15 | 340 | 0.8 | 50.4 | 84.8 |
| CE | 3.24 | 0.072 | 25.3 | 1 | 15 | 1007 | 15 | 360 | 0.6 | 57 | 82.8 |
| CE | 2.592 | 0.072 | 12 | 1 | 12 | 1020 | 12 | 340 | 1 | 49 | 86.7 |
| CE | 1.38 | 0.051 | 15.2 | 1 | 9 | 4543 | 9 | 370 | 0.6 | 46.5 | 83.3 |
| CE | 2.592 | 0.072 | 15 | 1 | 12 | 3789 | 12 | 360 | 0.8 | 50.3 | 83.7 |
| CE | 2.592 | 0.072 | 15 | 1 | 12 | 3789 | 12 | 360 | 0.8 | 47.1 | 86.8 |
| CE | 3.24 | 0.072 | 15 | 1 | 15 | 3789 | 15 | 360 | 1 | 46.3 | 87.8 |
| CE | 2.592 | 0.072 | 20.3 | 1 | 12 | 3617 | 12 | 340 | 0.6 | 48.5 | 79.8 |
| CE | 1.38 | 0.051 | 15.2 | 1 | 9 | 4543 | 9 | 370 | 0.6 | 46.3 | 83.1 |
| CE | 1.38 | 0.051 | 15.2 | 1 | 9 | 4543 | 9 | 370 | 0.6 | 46.2 | 83 |
| CE | 1.944 | 0.072 | 11.3 | 1 | 9 | 3789 | 9 | 340 | 0.8 | 48.4 | 83.2 |

TABLE 9-continued

Catalyst 3 (11.61W + 7.5V/12.42P@Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 0.922 | 0.034 | 9 | 1 | 9 | 3789 | 9 | 360 | 1 | 46.4 | 85.8 |
| CE | 1.38 | 0.051 | 15.2 | 1 | 9 | 4543 | 9 | 370 | 0.6 | 45 | 83.1 |
| CE | 1.38 | 0.051 | 15.2 | 1 | 9 | 4543 | 9 | 370 | 0.6 | 44 | 82.2 |
| CE | 2.592 | 0.072 | 12 | 1 | 12 | 3789 | 12 | 340 | 1 | 32 | 90 |
| CE | 3.24 | 0.072 | 18.8 | 1 | 15 | 3789 | 15 | 340 | 0.8 | 29.2 | 87.1 |

For the inventive operating windows, a positive effect on the selectivity of acrylic acid formation was found with comparably good carbon conversion (C).

TABLE 10

Catalyst 4 (7.5V + 8.93W + 0.576K + 11.53P/Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W1 | 0.96 | 0.04 | 6.67 | 1 | 8 | 816 | 8 | 360 | 1.2 | 68.5 | 78.3 |
| W1 | 1.2 | 0.04 | 8.33 | 1 | 10 | 816 | 10 | 360 | 1.2 | 63.7 | 81.3 |
| W1 | 2.16 | 0.072 | 10 | 1 | 10 | 816 | 10 | 360 | 1 | 68.2 | 82.9 |
| W1 | 1.944 | 0.072 | 9 | 1 | 9 | 1020 | 9 | 360 | 1 | 65.2 | 86.8 |
| W1 | 2.592 | 0.072 | 12 | 1 | 12 | 1020 | 12 | 380 | 1 | 67.6 | 80.7 |
| W1 | 1.433 | 0.053 | 9 | 1 | 9 | 1020 | 9 | 360 | 1 | 63 | 85.4 |
| W4 | 0.96 | 0.04 | 8 | 1 | 8 | 816 | 8 | 355 | 1 | 63.4 | 84.7 |
| W4 | 1.944 | 0.072 | 9 | 1 | 9 | 1020 | 9 | 350 | 1 | 60.8 | 85.6 |
| W1 | 1.2 | 0.04 | 10 | 1 | 10 | 816 | 10 | 360 | 1 | 59.6 | 83 |
| W1 | 0.922 | 0.034 | 9 | 1 | 9 | 1020 | 9 | 360 | 1 | 57.2 | 84.8 |
| W1 | 1.944 | 0.072 | 11.25 | 1 | 9 | 1020 | 9 | 380 | 0.8 | 68.6 | 78.9 |
| W3 | 3.24 | 0.072 | 18.75 | 1 | 15 | 3617 | 15 | 380 | 0.8 | 66 | 80 |
| W1 | 2.592 | 0.072 | 15 | 1 | 12 | 1020 | 12 | 360 | 0.8 | 60.6 | 85.8 |
| W1 | 2.592 | 0.072 | 15 | 1 | 12 | 1020 | 12 | 360 | 0.8 | 59.3 | 82.1 |
| CE | 1.944 | 0.072 | 15.2 | 1 | 9 | 3617 | 9 | 360 | 0.6 | 29.7 | 61.5 |
| CE | 3.24 | 0.072 | 25.3 | 1 | 15 | 959 | 15 | 360 | 0.6 | 35.6 | 58.2 |
| CE | 1.38 | 0.051 | 15.2 | 1 | 9 | 4346 | 9 | 370 | 0.6 | 31.2 | 68.9 |
| CE |  | 0 | 15.2 | 1 | 9 |  | 9 | 370 | 0.6 | 31.2 | 68.9 |
| CE | 1.38 | 0.051 | 15.2 | 1 | 9 | 4346 | 9 | 370 | 0.6 | 32.5 | 68.8 |
| CE | 2.16 | 0.08 | 15.2 | 1 | 9 | 2768 | 9 | 360 | 0.6 | 36.9 | 62.2 |
| CE | 1.38 | 0.051 | 15.2 | 1 | 9 | 4346 | 9 | 370 | 0.6 | 33.5 | 69.2 |
| CE | 1.38 | 0.051 | 15.2 | 1 | 9 | 4346 | 9 | 370 | 0.6 | 34.7 | 69.5 |
| CE | 2.592 | 0.072 | 20.3 | 1 | 12 | 959 | 12 | 340 | 0.6 | 46.1 | 54 |
| CE | 1.44 | 0.04 | 10 | 1 | 12 | 2894 | 12 | 360 | 1.2 | 84.8 | 77.2 |
| CE | 1.38 | 0.051 | 15.2 | 1 | 9 | 4346 | 9 | 370 | 0.6 | 36.2 | 70.2 |
| CE | 2.16 | 0.072 | 10 | 1 | 10 | 2894 | 10 | 360 | 1 | 72 | 68.2 |
| CE | 2.592 | 0.072 | 20.3 | 1 | 12 | 3617 | 12 | 380 | 0.6 | 41.7 | 65.9 |
| CE | 1.2 | 0.04 | 10 | 1 | 10 | 2894 | 10 | 360 | 1 | 50 | 86.7 |
| CE | 0.96 | 0.04 | 6.67 | 1 | 8 | 2894 | 8 | 360 | 1.2 | 51.3 | 83.7 |
| CE | 1.96 | 0.05764706 | 1.39 | 15.2 | 12.5 | 1020 | 9 | 390 | 0.6 | 58.6 | 67.1 |
| CE | 0.9 | 0.04 | 0.75 | 15.2 | 6.75 | 1020 | 9 | 390 | 0.6 | 55.4 | 72.3 |
| CE | 1.944 | 0.072 | 11.25 | 1 | 9 | 1020 | 9 | 340 | 0.8 | 59 | 80.9 |
| CE | 1.96 | 0.04 | 1.25 | 23.64 | 17.5 | 1020 | 14 | 390 | 0.6 | 46.1 | 73.3 |
| CE | 0.96 | 0.04 | 8 | 1 | 8 | 2894 | 8 | 355 | 1 | 51.4 | 87.2 |
| CE | 1.433 | 0.053 | 9 | 1 | 9 | 3617 | 9 | 360 | 1 | 50.6 | 84.8 |
| CE | 1.944 | 0.072 | 9 | 1 | 9 | 2894 | 9 | 350 | 1 | 51.9 | 81.8 |
| CE | 1.944 | 0.072 | 9 | 1 | 9 | 3617 | 9 | 350 | 1 | 51 | 83.2 |
| CE | 2.52 | 0.072 | 0.75 | 23.64 | 10.5 | 1020 | 14 | 390 | 0.6 | 64.9 | 75.1 |
| CE | 2.592 | 0.072 | 15 | 1 | 12 | 3617 | 12 | 360 | 0.8 | 45.6 | 86 |
| CE | 3.24 | 0.072 | 18.75 | 1 | 15 | 1020 | 15 | 340 | 0.8 | 44.7 | 87.2 |
| CE | 0.9 | 0.04 | 0.75 | 15.2 | 6.75 | 1020 | 9 | 390 | 0.6 | 59.0 | 63.9 |
| CE | 2.33 | 0.09456169 | 1.1 | 13 | 8.47 | 3789 | 7.7 | 350 | 0.6 | 34.4 | 83.1 |
| CE | 2.33 | 0.06881276 | 1.70 | 13 | 13.08 | 3789 | 7.7 | 350 | 0.6 | 29.7 | 84.7 |
| CE | 0.922 | 0.034 | 9 | 1 | 9 | 3617 | 9 | 360 | 1 | 44.6 | 85.8 |
| CE | 1.26 | 0.04 | 1.25 | 15.2 | 11.25 | 3789 | 9 | 350 | 0.6 | 33.1 | 84.3 |
| CE | 1.4 | 0.04 | 0.75 | 23.64 | 10.5 | 3789 | 14 | 350 | 0.6 | 30.0 | 80.0 |
| CE | 1.62 | 0.072 | 0.75 | 15.2 | 6.75 | 3789 | 9 | 350 | 0.6 | 39.1 | 80.1 |
| CE | 1.944 | 0.072 | 11.25 | 1 | 9 | 3617 | 9 | 340 | 0.8 | 43.5 | 84.8 |
| CE | 2.592 | 0.072 | 15 | 1 | 12 | 3617 | 12 | 360 | 0.8 | 39.6 | 88.7 |
| CE | 2.592 | 0.072 | 12 | 1 | 12 | 1020 | 12 | 340 | 1 | 37.5 | 89.9 |
| CE | 3.24 | 0.072 | 15 | 1 | 15 | 3617 | 15 | 360 | 1 | 37.6 | 89.5 |
| CE | 3.528 | 0.072 | 1.25 | 23.64 | 17.5 | 3789 | 14 | 350 | 0.6 | 38.4 | 79.6 |

TABLE 10-continued

Catalyst 4 (7.5V + 8.93W + 0.576K + 11.53P/Q20C)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 3.24 | 0.072 | 18.75 | 1 | 15 | 3617 | 15 | 340 | 0.8 | 23.8 | 88.0 |
| CE | 2.592 | 0.072 | 12 | 1 | 12 | 3617 | 12 | 340 | 1 | 21.5 | 93.3 |

For the inventive operating windows, a positive effect on the carbon conversion (C) was found with comparably good or enhanced selectivity of acrylic acid formation.

TABLE 11

Catalyst 5 (11.4V + 3.8W + 7Bi + 12.7P; unsupported catalyst)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 3 | 0.111 | 9 | 1 | 9 | 4681 | 9 | 320 | 1 | 16.1 | 84.7 |
| CE | 3 | 0.111 | 9 | 1 | 9 | 4681 | 9 | 350 | 1 | 33.1 | 85.3 |
| CE | 3 | 0.111 | 9 | 1 | 9 | 4681 | 9 | 370 | 1 | 40.2 | 82.9 |
| CE | 3 | 0.111 | 9 | 1 | 9 | 788 | 9 | 320 | 1 | 45.2 | 82.8 |
| CE | 3 | 0.111 | 9 | 1 | 9 | 1592 | 9 | 320 | 1 | 41.7 | 84 |
| CE | 3 | 0.067 | 15 | 1 | 15 | 4681 | 15 | 320 | 1 | 6.9 | 84 |
| CE | 3 | 0.067 | 15 | 1 | 15 | 4681 | 15 | 350 | 1 | 16.6 | 84 |
| CE | 3 | 0.067 | 15 | 1 | 15 | 1592 | 15 | 320 | 1 | 22.8 | 84 |
| CE | 3 | 0.067 | 15 | 1 | 15 | 4681 | 15 | 370 | 1 | 25 | 84.4 |
| CE | 3 | 0.067 | 15 | 1 | 15 | 788 | 15 | 320 | 1 | 25.8 | 83.5 |
| CE | 1.5 | 0.056 | 9 | 1 | 9 | 4681 | 9 | 320 | 1 | 12.1 | 77.9 |
| CE | 1.5 | 0.056 | 9 | 1 | 9 | 1530 | 9 | 320 | 1 | 21.6 | 75.4 |
| CE | 1.5 | 0.056 | 9 | 1 | 9 | 804 | 9 | 320 | 1 | 27.5 | 74 |
| CE | 1.5 | 0.056 | 9 | 1 | 9 | 4681 | 9 | 350 | 1 | 30.7 | 87.9 |
| CE | 1.5 | 0.033 | 15 | 1 | 15 | 4681 | 15 | 320 | 1 | 7.6 | 86.4 |
| CE | 1.5 | 0.033 | 15 | 1 | 15 | 4681 | 15 | 350 | 1 | 15.3 | 86.7 |
| CE | 1.5 | 0.033 | 15 | 1 | 15 | 1530 | 15 | 320 | 1 | 16.9 | 85 |
| CE | 1.5 | 0.033 | 15 | 1 | 15 | 804 | 15 | 320 | 1 | 24 | 86.6 |
| CE | 1.5 | 0.033 | 15 | 1 | 15 | 4681 | 15 | 370 | 1 | 25.5 | 87.5 |
| CE | 0.5 | 0.011 | 15 | 1 | 15 | 804 | 15 | 390 | 1 | 21.4 | 83.3 |
| CE | 0.5 | 0.011 | 15 | 1 | 15 | 4681 | 15 | 320 | 1 | 6.9 | 87.2 |
| CE | 0.5 | 0.011 | 15 | 1 | 15 | 4681 | 15 | 350 | 1 | 17 | 92.2 |
| CE | 0.5 | 0.011 | 15 | 1 | 15 | 4681 | 15 | 370 | 1 | 19.1 | 91.5 |
| CE | 0.5 | 0.011 | 15 | 1 | 15 | 1592 | 15 | 320 | 1 | 20.3 | 90.4 |
| CE | 0.5 | 0.011 | 15 | 1 | 15 | 788 | 15 | 320 | 1 | 22.5 | 89.6 |
| CE | 0.5 | 0.011 | 15 | 1 | 15 | 804 | 15 | 350 | 1 | 28.2 | 89.7 |
| CE | 0.5 | 0.011 | 15 | 1 | 15 | 1530 | 15 | 350 | 1 | 25.3 | 89.6 |
| CE | 0.5 | 0.011 | 15 | 1 | 15 | 788 | 15 | 370 | 1 | 25.6 | 87.4 |
| CE | 0.5 | 0.011 | 15 | 1 | 15 | 1592 | 15 | 370 | 1 | 24.2 | 87.9 |
| CE | 0.5 | 0.011 | 15 | 1 | 15 | 1530 | 15 | 390 | 1 | 20.1 | 84.1 |
| CE | 0.5 | 0.011 | 15 | 1 | 15 | 4681 | 15 | 390 | 1 | 19.1 | 85.3 |
| CE | 0.5 | 0.019 | 9 | 1 | 9 | 4681 | 9 | 320 | 1 | 7.9 | 75.5 |
| CE | 0.5 | 0.019 | 9 | 1 | 9 | 1592 | 9 | 320 | 1 | 13.5 | 73.4 |
| CE | 0.5 | 0.019 | 9 | 1 | 9 | 788 | 9 | 320 | 1 | 15.6 | 74.3 |
| CE | 0.5 | 0.019 | 9 | 1 | 9 | 1530 | 9 | 390 | 1 | 27.5 | 80.7 |
| CE | 0.5 | 0.019 | 9 | 1 | 9 | 804 | 9 | 390 | 1 | 29.8 | 79.2 |
| CE | 0.5 | 0.019 | 9 | 1 | 9 | 4681 | 9 | 350 | 1 | 30 | 90 |
| CE | 0.5 | 0.019 | 9 | 1 | 9 | 4681 | 9 | 370 | 1 | 30.6 | 88.1 |
| CE | 0.5 | 0.019 | 9 | 1 | 9 | 4681 | 9 | 390 | 1 | 25.3 | 81.8 |
| W2 | 1.5 | 0.033 | 15 | 1 | 15 | 804 | 15 | 370 | 1 | 44.4 | 86.5 |
| W2 | 1.5 | 0.033 | 15 | 1 | 15 | 1530 | 15 | 370 | 1 | 40.5 | 87.1 |
| W2 | 1.5 | 0.033 | 15 | 1 | 15 | 788 | 15 | 390 | 1 | 41.8 | 83.1 |
| W2 | 1.5 | 0.033 | 15 | 1 | 15 | 788 | 15 | 350 | 1 | 39.4 | 87.5 |
| W2 | 1.5 | 0.033 | 15 | 1 | 15 | 1592 | 15 | 390 | 1 | 40.7 | 83.4 |
| W2 | 1.5 | 0.033 | 15 | 1 | 15 | 1592 | 15 | 350 | 1 | 31.5 | 87.8 |
| W3 | 1.5 | 0.033 | 15 | 1 | 15 | 4681 | 15 | 390 | 1 | 33.1 | 85.5 |
| W1 | 0.92 | 0.034 | 9 | 1 | 9 | 1047 | 9 | 360 | 1 | 50.3 | 86.3 |
| W1 | 1.43 | 0.053 | 9 | 1 | 9 | 1047 | 9 | 360 | 1 | 58.5 | 85.4 |
| W1 | 1.5 | 0.056 | 9 | 1 | 9 | 804 | 9 | 370 | 1 | 58.8 | 83.5 |
| W1 | 1.5 | 0.056 | 9 | 1 | 9 | 1530 | 9 | 370 | 1 | 56.9 | 84.4 |
| W3 | 1.5 | 0.056 | 9 | 1 | 9 | 4681 | 9 | 390 | 1 | 41.4 | 82.4 |
| W4 | 1.5 | 0.056 | 9 | 1 | 9 | 788 | 9 | 350 | 1 | 58.8 | 85.4 |
| W4 | 1.5 | 0.056 | 9 | 1 | 9 | 1592 | 9 | 350 | 1 | 51.9 | 86.2 |
| W2 | 3 | 0.067 | 15 | 1 | 15 | 804 | 15 | 390 | 1 | 58.6 | 80.6 |
| W2 | 3 | 0.067 | 15 | 1 | 15 | 788 | 15 | 370 | 1 | 54.6 | 83.2 |
| W2 | 3 | 0.067 | 15 | 1 | 15 | 1530 | 15 | 390 | 1 | 56 | 81 |

TABLE 11-continued

Catalyst 5 (11.4V + 3.8W + 7Bi + 12.7P; unsupported catalyst)

| Operating window | Gas O2 [%] | O2/TOC | Gas H2O [%] | ACE/FA | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W2 | 3 | 0.067 | 15 | 1 | 15 | 1592 | 15 | 370 | 1 | 44.1 | 84 |
| W2 | 3 | 0.067 | 15 | 1 | 15 | 804 | 15 | 350 | 1 | 41.2 | 84.1 |
| W4 | 1.94 | 0.072 | 9 | 1 | 9 | 1047 | 9 | 350 | 1 | 56.6 | 84.8 |

For the inventive operating windows, a positive effect on the carbon conversion (C) was found with comparably good selectivity of acrylic acid formation.

TABLE 12

Catalyst 6 (7.5V + 8.93W + 2.045La + 11.53P/Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W4 | 2.33 | 0.095 | 1.1 | 13 | 8.47 | 1020 | 7.7 | 350 | 0.6 | 57.5 | 84.1 |
| W4 | 1.62 | 0.072 | 0.75 | 15.2 | 6.75 | 1020 | 9 | 350 | 0.6 | 58 | 83.9 |
| W4 | 1.62 | 0.072 | 0.75 | 15.2 | 6.75 | 1020 | 9 | 350 | 0.6 | 59.5 | 81.6 |
| W4 | 1.62 | 0.072 | 0.75 | 15.2 | 6.75 | 1020 | 9 | 350 | 0.6 | 68.3 | 79.8 |
| W4 | 2.52 | 0.072 | 0.75 | 14 | 10.5 | 1020 | 14 | 350 | 1 | 61.6 | 84.3 |
| W4 | 0.9 | 0.04 | 0.75 | 9 | 6.75 | 1020 | 9 | 350 | 1 | 59.1 | 84 |
| W4 | 0.9 | 0.04 | 0.75 | 9 | 6.75 | 1020 | 9 | 350 | 1 | 58.1 | 83.1 |
| W3 | 1.62 | 0.072 | 0.75 | 9 | 6.75 | 3789 | 9 | 390 | 1 | 65 | 76.1 |
| W3 | 1.62 | 0.072 | 0.75 | 9 | 6.75 | 3789 | 9 | 390 | 1 | 56.5 | 76.2 |
| W4 | 0.9 | 0.04 | 0.75 | 9 | 6.75 | 1020 | 9 | 350 | 1 | 61.5 | 86 |
| W4 | 0.9 | 0.04 | 0.75 | 9 | 6.75 | 1020 | 9 | 350 | 1 | 59.2 | 84.7 |
| W4 | 0.9 | 0.04 | 0.75 | 9 | 6.75 | 1020 | 9 | 350 | 1 | 58.9 | 84.6 |
| CE | 3.528 | 0.072 | 1.25 | 23.64 | 17.5 | 1020 | 14 | 350 | 0.6 | 51.4 | 80.9 |
| CE | 1.26 | 0.04 | 1.25 | 15.2 | 11.25 | 1020 | 9 | 350 | 0.6 | 52 | 85.4 |
| CE | 1.96 | 0.04 | 1.25 | 14 | 17.5 | 1020 | 14 | 350 | 1 | 49.7 | 87.1 |
| CE | 1.96 | 0.058 | 1.39 | 15.2 | 12.5 | 1020 | 9 | 390 | 0.6 | 58.6 | 67.1 |
| CE | 0.9 | 0.04 | 0.75 | 15.2 | 6.75 | 1020 | 9 | 390 | 0.6 | 55.4 | 72.3 |
| CE | 1.96 | 0.04 | 1.25 | 23.64 | 17.5 | 1020 | 14 | 390 | 0.6 | 46.1 | 73.3 |
| CE | 2.52 | 0.072 | 0.75 | 23.64 | 10.5 | 1020 | 14 | 390 | 0.6 | 64.9 | 75.1 |
| CE | 0.9 | 0.04 | 0.75 | 15.2 | 6.75 | 1020 | 9 | 390 | 0.6 | 59 | 63.9 |
| CE | 1.26 | 0.04 | 1.25 | 9 | 11.25 | 1020 | 9 | 390 | 1 | 42.4 | 62.1 |
| CE | 1.26 | 0.04 | 1.25 | 9 | 11.25 | 1020 | 9 | 390 | 1 | 40.7 | 65.6 |
| CE | 3.528 | 0.072 | 1.25 | 14 | 17.5 | 1020 | 14 | 390 | 1 | 52 | 71.3 |
| CE | 2.33 | 0.095 | 1.1 | 13 | 8.47 | 3789 | 7.7 | 350 | 0.6 | 34.4 | 83.1 |
| CE | 2.33 | 0.069 | 1.7 | 13 | 13.08 | 3789 | 7.7 | 350 | 0.6 | 29.7 | 84.7 |
| CE | 1.26 | 0.04 | 1.25 | 15.2 | 11.25 | 3789 | 9 | 350 | 0.6 | 33.1 | 84.3 |
| CE | 1.4 | 0.04 | 0.75 | 23.64 | 10.5 | 3789 | 14 | 350 | 0.6 | 30 | 80 |
| CE | 1.62 | 0.072 | 0.75 | 15.2 | 6.75 | 3789 | 9 | 350 | 0.6 | 39.1 | 80.1 |
| CE | 3.528 | 0.072 | 1.25 | 23.64 | 17.5 | 3789 | 14 | 350 | 0.6 | 38.4 | 79.6 |
| CE | 1.62 | 0.072 | 0.75 | 15.2 | 6.75 | 3789 | 9 | 350 | 0.6 | 48 | 79.8 |
| CE | 0.9 | 0.04 | 0.75 | 9 | 6.75 | 3789 | 9 | 350 | 1 | 45.8 | 88.5 |
| CE | 2.268 | 0.072 | 1.25 | 9 | 11.25 | 3789 | 9 | 350 | 1 | 43.5 | 87 |
| CE | 1.96 | 0.04 | 1.25 | 14 | 17.5 | 3789 | 14 | 350 | 1 | 35.6 | 89.4 |
| CE | 2.52 | 0.072 | 0.75 | 14 | 10.5 | 3789 | 14 | 350 | 1 | 56.6 | 68.9 |
| CE | 0.9 | 0.04 | 0.75 | 9 | 6.75 | 3789 | 9 | 350 | 1 | 46.2 | 87.4 |
| CE | 0.9 | 0.04 | 0.75 | 9 | 6.75 | 3789 | 9 | 350 | 1 | 46.4 | 87.2 |
| CE | 0.9 | 0.04 | 0.75 | 9 | 6.75 | 3789 | 9 | 350 | 1 | 49.2 | 86.6 |
| CE | 0.9 | 0.04 | 0.75 | 9 | 6.75 | 3789 | 9 | 350 | 1 | 46.8 | 86.6 |
| CE | 0.9 | 0.04 | 0.75 | 9 | 6.75 | 3789 | 9 | 350 | 1 | 46.6 | 85.5 |
| CE | 2.33 | 0.069 | 1.7 | 13 | 13.08 | 1020 | 7.7 | 350 | 0.6 | 46.9 | 85.2 |
| CE | 2.33 | 0.095 | 1.1 | 13 | 8.47 | 3789 | 7.7 | 390 | 0.6 | 45.7 | 80.2 |
| CE | 0.9 | 0.04 | 0.75 | 15.2 | 6.75 | 3789 | 9 | 390 | 0.6 | 54.3 | 76.5 |
| CE | 1.96 | 0.04 | 1.25 | 23.64 | 17.5 | 3789 | 14 | 390 | 0.6 | 42.9 | 79.7 |
| CE | 1.96 | 0.058 | 1.39 | 15.2 | 12.5 | 3789 | 9 | 390 | 0.6 | 43.7 | 77.2 |
| CE | 2.268 | 0.072 | 1.25 | 15.2 | 11.25 | 1020 | 9 | 390 | 0.6 | 61.6 | 73.7 |

TABLE 12-continued

Catalyst 6 (7.5V + 8.93W + 2.045La + 11.53P/Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 1.26  | 0.04  | 1.25 | 9  | 11.25 | 3789 | 9  | 390 | 1 | 32.6 | 73.2 |
| CE | 3.528 | 0.072 | 1.25 | 14 | 17.5  | 3789 | 14 | 390 | 1 | 49.6 | 76.6 |

For the inventive operating windows, a positive effect on the carbon conversion (C) was found with comparably good selectivity of acrylic acid formation.

TABLE 13

Catalyst 7 (8.12W + 7.5V/11.3P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 0.102 | 1.00 | 15.2 | 9    | 1249 | 9    | 370 | 0.6 | 61.6 | 81.6 |
| W5 | 1.38 | 0.051 | 1.00 | 15.2 | 9    | 1249 | 9    | 370 | 0.6 | 58.2 | 84.7 |
| W5 | 2.75 | 0.068 | 1.00 | 22.8 | 13.5 | 1249 | 13.5 | 370 | 0.6 | 58.8 | 82.3 |
| W5 | 2.75 | 0.087 | 0.67 | 22.8 | 9    | 1249 | 13.5 | 370 | 0.6 | 57.9 | 80.3 |
| W5 | 1.38 | 0.034 | 1.00 | 22.8 | 13.5 | 1249 | 13.5 | 370 | 0.6 | 51.8 | 83.8 |
| W5 | 2.75 | 0.051 | 1.00 | 30.4 | 18   | 1249 | 18   | 370 | 0.6 | 51.2 | 81.3 |
| CE | 1.38 | 0.038 | 1.50 | 15.2 | 13.5 | 1249 | 9    | 370 | 0.6 | 46.2 | 80   |
| CE | 1.38 | 0.034 | 1.00 | 22.8 | 13.5 | 1249 | 13.5 | 390 | 0.6 | 44.8 | 71.3 |
| CE | 2.75 | 0.076 | 1.50 | 15.2 | 13.5 | 1249 | 9    | 370 | 0.6 | 56   | 79   |

For the inventive operating window, a positive effect on the carbon conversion (C) and a positive effect on the selectivity of acrylic acid formation were found.

TABLE 14

Catalyst 8 (8.93W + 7.5V/11.3P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 0.102 | 1     | 15.2 | 9    | 1265 | 9    | 370 | 0.6 | 66.4 | 79.8 |
| W5 | 1.38 | 0.051 | 1     | 15.2 | 9    | 1265 | 9    | 370 | 0.6 | 60.4 | 83.5 |
| W5 | 2.75 | 0.068 | 1     | 22.8 | 13.5 | 1265 | 13.5 | 370 | 0.6 | 61.8 | 81.3 |
| W5 | 2.75 | 0.087 | 0.667 | 22.8 | 9    | 1265 | 13.5 | 370 | 0.6 | 62.4 | 79.2 |
| W5 | 1.38 | 0.044 | 0.667 | 22.8 | 9    | 1265 | 13.5 | 370 | 0.6 | 53.9 | 80.4 |
| W5 | 1.38 | 0.034 | 1     | 22.8 | 13.5 | 1265 | 13.5 | 370 | 0.6 | 51   | 82   |
| CE | 2.75 | 0.051 | 1     | 30.4 | 18   | 1265 | 18   | 370 | 0.6 | 50.8 | 79.5 |
| CE | 1.38 | 0.038 | 1.5   | 15.2 | 13.5 | 1265 | 9    | 370 | 0.6 | 45.8 | 78.8 |
| CE | 1.38 | 0.034 | 1     | 22.8 | 13.5 | 1265 | 13.5 | 390 | 0.6 | 44.2 | 70.5 |
| CE | 2.75 | 0.076 | 1.5   | 15.2 | 13.5 | 1265 | 9    | 370 | 0.6 | 56.8 | 77.7 |

For the inventive operating windows, a positive effect on the carbon conversion (C) and the selectivity of acrylic acid formation was found.

TABLE 15

Catalyst 9 (9.74W + 7.5V/11.3P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 0.10 | 1     | 15.2 | 9    | 1281 | 9    | 370 | 0.6 | 65.9 | 80.4 |
| W5 | 2.75 | 0.07 | 1     | 22.8 | 13.5 | 1281 | 13.5 | 370 | 0.6 | 62.1 | 81.9 |
| W5 | 1.38 | 0.05 | 1     | 15.2 | 9    | 1281 | 9    | 370 | 0.6 | 60.2 | 83.9 |
| W5 | 2.75 | 0.09 | 0.667 | 22.8 | 9    | 1281 | 13.5 | 370 | 0.6 | 62.3 | 79.7 |
| W5 | 1.38 | 0.04 | 0.667 | 22.8 | 9    | 1281 | 13.5 | 370 | 0.6 | 54.1 | 81.1 |
| W5 | 1.38 | 0.03 | 1     | 22.8 | 13.5 | 1281 | 13.5 | 370 | 0.6 | 51.3 | 82.7 |

TABLE 15-continued

Catalyst 9 (9.74W + 7.5V/11.3P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| CE | 2.75 | 0.05 | 1   | 30.4 | 18   | 1281 | 18   | 370 | 0.6 | 51.1 | 80.3 |
| CE | 1.38 | 0.04 | 1.5 | 15.2 | 13.5 | 1281 | 9    | 370 | 0.6 | 45.7 | 79.3 |
| CE | 1.38 | 0.03 | 1   | 22.8 | 13.5 | 1281 | 13.5 | 390 | 0.6 | 43.4 | 71.2 |
| CE | 2.75 | 0.08 | 1.5 | 15.2 | 13.5 | 1281 | 9    | 370 | 0.6 | 57.1 | 78.4 |

For the inventive operating window, a positive effect on the carbon conversion (C) and the selectivity of acrylic acid formation was found.

TABLE 16

Catalyst 10 (11.61W + 7.5V/11.3P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 0.061 | 1.00 | 15.2 | 9    | 1249 | 9    | 370 | 0.6 | 66.9 | 80.5 |
| W5 | 2.75 | 0.05  | 1.00 | 22.8 | 13.5 | 1249 | 13.5 | 370 | 0.6 | 62.9 | 82   |
| W5 | 2.75 | 0.051 | 0.67 | 22.8 | 9    | 1249 | 13.5 | 370 | 0.6 | 63.5 | 80   |
| W5 | 1.38 | 0.062 | 1.00 | 15.2 | 9    | 1249 | 9    | 370 | 0.6 | 60   | 83.7 |
| W5 | 1.38 | 0.05  | 0.67 | 22.8 | 9    | 1249 | 13.5 | 370 | 0.6 | 54.4 | 81.2 |
| W5 | 1.38 | 0.048 | 1.00 | 22.8 | 13.5 | 1249 | 13.5 | 370 | 0.6 | 50.9 | 82.5 |
| CE | 2.75 | 0.029 | 1.00 | 30.4 | 18   | 1249 | 18   | 370 | 0.6 | 51.5 | 80.2 |
| CE | 1.38 | 0.055 | 1.50 | 15.2 | 13.5 | 1249 | 9    | 370 | 0.6 | 45.3 | 79   |
| CE | 2.75 | 0.054 | 1.50 | 15.2 | 13.5 | 1249 | 9    | 370 | 0.6 | 57.4 | 78.3 |

For the inventive operating windows, a positive effect on the carbon conversion (C) and the selectivity of acrylic acid formation was found.

TABLE 17

Catalyst 11 (8.93W + 7.5V/11.53P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 2.372 | 1.00 | 15.2 | 9    | 1234 | 9    | 370 | 0.6 | 64.1 | 81.6 |
| W5 | 2.75 | 1.172 | 1.00 | 22.8 | 13.5 | 1234 | 13.5 | 370 | 0.6 | 61.3 | 82.6 |
| W5 | 1.38 | 2.423 | 1.00 | 15.2 | 9    | 1234 | 9    | 370 | 0.6 | 59.6 | 84.7 |
| W5 | 2.75 | 1.649 | 0.67 | 22.8 | 9    | 1234 | 13.5 | 370 | 0.6 | 60.4 | 80.7 |
| W5 | 1.38 | 1.693 | 0.67 | 22.8 | 9    | 1234 | 13.5 | 370 | 0.6 | 54.6 | 82.2 |
| W5 | 1.38 | 1.205 | 1.00 | 22.8 | 13.5 | 1234 | 13.5 | 370 | 0.6 | 51.5 | 83.3 |
| CE | 2.75 | 0.571 | 1.00 | 30.4 | 18   | 1234 | 18   | 370 | 0.6 | 51.3 | 80.8 |
| CE | 1.38 | 1.692 | 1.50 | 15.2 | 13.5 | 1234 | 9    | 370 | 0.6 | 45.6 | 79.4 |
| CE | 1.38 | 1.205 | 1.00 | 22.8 | 13.5 | 1234 | 13.5 | 390 | 0.6 | 42.5 | 71   |
| CE | 2.75 | 1.654 | 1.50 | 15.2 | 13.5 | 1234 | 9    | 370 | 0.6 | 57.3 | 79.2 |

For the inventive operating windows, a positive effect on the carbon conversion (C) and the selectivity of acrylic acid formation was found.

TABLE 18

Catalyst 12 (11.61W + 7.5V/12.42P@Q20C)

| Operating window | Gas O2 [%] | O2/TOC | ACE/FA | Gas H2O [%] | Gas ACE [%] | GHSV [h−1] | Gas FA [%] | Temperature [° C.] | FA/H2O | Carbon conversion (C) [%] | S(ACR) [%] |
|---|---|---|---|---|---|---|---|---|---|---|---|
| W5 | 2.75 | 0.062 | 1.00 | 15.2 | 9    | 1249 | 9    | 370 | 0.6 | 60.5 | 83.9 |
| W5 | 2.75 | 0.051 | 1.00 | 22.8 | 13.5 | 1249 | 13.5 | 370 | 0.6 | 59.5 | 84   |
| W5 | 2.75 | 0.053 | 0.67 | 22.8 | 9    | 1249 | 13.5 | 370 | 0.6 | 58.1 | 82.5 |
| W5 | 1.38 | 0.065 | 1.00 | 15.2 | 9    | 1249 | 9    | 370 | 0.6 | 55.7 | 85.9 |

TABLE 18-continued

Catalyst 12 (11.61W + 7.5V/12.42P@Q20C)

| Operating window | Gas O2 [%] | O2/ TOC | ACE/FA | Gas H2O [%] | Gas ACE [%] | GHSV [h-1] | Gas FA [%] | Temperature [° C.] | FA/H2O | Carbon conversion (C) [%] | S(ACR) [%] |
|---|---|---|---|---|---|---|---|---|---|---|---|
| W5 | 1.38 | 0.053 | 0.67 | 22.8 | 9 | 1249 | 13.5 | 370 | 0.6 | 55.2 | 84.3 |
| W5 | 1.38 | 0.049 | 1.00 | 22.8 | 13.5 | 1249 | 13.5 | 370 | 0.6 | 51.9 | 84.8 |
| CE | 2.75 | 0.031 | 1.00 | 30.4 | 18 | 1249 | 18 | 370 | 0.6 | 52.1 | 82.4 |
| CE | 1.38 | 0.057 | 1.50 | 15.2 | 13.5 | 1249 | 9 | 370 | 0.6 | 45.4 | 80.4 |
| CE | 1.38 | 0.047 | 1.00 | 22.8 | 13.5 | 1249 | 13.5 | 390 | 0.6 | 41.7 | 72.4 |
| CE | 2.75 | 0.056 | 1.50 | 15.2 | 13.5 | 1249 | 9 | 370 | 0.6 | 56.6 | 80.4 |

For the inventive operating windows, a positive effect on the carbon conversion (C) and on the selectivity of acrylic acid formation was found.

TABLE 19

Catalyst 13 (11.15W + 8.43V/12.42P@Q20C)

| Operating window | O2/ TOC | Gas O2 [%] | ACE/FA | Gas H2O [%] | Gas ACE [%] | GHSV [h-1] | Gas FA [%] | Temperature [° C.] | FA/H2O | Carbon conversion (C) [%] | S(ACR) [%] |
|---|---|---|---|---|---|---|---|---|---|---|---|
| W5 | 0.063 | 15.2 | 1.00 | 15.2 | 9 | 1265 | 9 | 370 | 0.6 | 67 | 80.2 |
| W5 | 0.052 | 22.8 | 1.00 | 22.8 | 13.5 | 1265 | 13.5 | 370 | 0.6 | 62.7 | 81.5 |
| W5 | 0.064 | 15.2 | 1.00 | 15.2 | 9 | 1265 | 9 | 370 | 0.6 | 59.9 | 83.5 |
| W5 | 0.048 | 22.8 | 1.00 | 22.8 | 13.5 | 1265 | 13.5 | 370 | 0.6 | 49.4 | 82 |
| W5 | 2.962 | 22.8 | 0.67 | 15.2 | 9 | 1265 | 13.5 | 370 | 0.6 | 52 | 80.7 |
| W5 | 0.052 | 22.8 | 0.67 | 15.2 | 9 | 1265 | 13.5 | 370 | 0.6 | 63.1 | 79.6 |
| CE | 0.056 | 15.2 | 1.50 | 15.2 | 13.5 | 1265 | 9 | 370 | 0.6 | 56.9 | 78.1 |
| CE | 0.057 | 15.2 | 1.50 | 15.2 | 13.5 | 1265 | 9 | 370 | 0.6 | 44.1 | 78.8 |
| CE | 0.031 | 30.4 | 1.00 | 30.4 | 18 | 1265 | 18 | 370 | 0.6 | 50.3 | 79.8 |

For the inventive operating windows, a positive effect on the carbon conversion (C) and the selectivity of acrylic acid formation was found.

The invention claimed is:

1. A process for preparing acrylic acid from formaldehyde and acetic acid, comprising
   (i) providing a gaseous stream S1 comprising formaldehyde, acetic acid, oxygen and water, where the formaldehyde content of stream S1 is in the range from 8% to 18% by volume, based on the total volume of stream S1, the ratio of the volumes of acetic acid to formaldehyde is in the range from 0.6:1 to 1.1:1, the molar ratio of oxygen from gaseous stream S1 to the total amount of organic carbon is in the range from 0.02:1 to 0.15:1 and the ratio of the volumes of formaldehyde to water is in the range from 0.8:1 to 1.3:1;
   (ii) contacting stream S1 with an aldol condensation catalyst in a reaction zone to obtain a gaseous stream S2 comprising acrylic acid, wherein the aldol condensation catalyst in (ii) comprises a vanadium phosphorus oxide $V_xP_yO_z$ wherein the x:y weight ratio is in the range from 1:0.5 to 1:5, and the x:z weight ratio is in the range from 1:0.1 to 1:10.

2. The process according to claim 1, wherein the space velocity GHSV in the reaction zone is in the range from 800 to 6500 $h^{-1}$ and is defined as the total volume flow rate of stream S1, in $m^3/h$, per unit catalyst volume, in $m^3$, under standard conditions at 0° C.; absolute pressure 1.013 bar.

3. The process according to claim 1, wherein the temperature in the reaction zone, defined as the temperature at which stream S1 is contacted with the aldol condensation catalyst, is in the range from 350 to 400° C.

4. The process according to claim 1, wherein the formaldehyde content of stream S1 is in the range from 8% to 14% by volume, based on the total volume of stream S1.

5. The process according to claim 1, wherein the ratio of the volumes of acetic acid to formaldehyde in stream S1 is in the range from 0.9:1 to 1.1:1.

6. The process according to claim 1, wherein the space velocity GHSV in the reaction zone is in the range from 800 to 2600 $h^{-1}$.

7. The process according to claim 1, wherein the temperature in the reaction zone is in the range from 360 to 380° C.

8. The process according to claim 1, wherein the formaldehyde content of stream S1 is in the range from 8% to 14% by volume, based on the total volume of stream S1, the ratio of the volumes of acetic acid to formaldehyde in stream S1 is in the range from 0.9:1 to 1.1:1, the molar ratio of oxygen to the total amount of organic carbon is in the range from 0.02:1 to 0.15:1, the ratio of the volumes of formaldehyde to water is in the range from 0.8:1 to 1.3:1, the space velocity GHSV in the reaction zone is in the range from 800 to 2600 $h^{-1}$ and the temperature in the reaction zone is in the range from 360 to 380° C.

9. The process according to claim 1, wherein the ratio of the volumes of acetic acid to formaldehyde in stream S1 is in the range from 0.75:1 to 1.1:1.

10. The process according to claim 1, wherein the space velocity GHSV in the reaction zone is in the range from 1600 to 6500 $h^{-1}$.

11. The process according to claim 1, wherein the temperature in the reaction zone is in the range from 380 to 400° C.

12. The process according to claim 1, wherein the formaldehyde content of stream S1 is in the range from 8% to 18% by volume, based on the total volume of stream S1, the ratio of the volumes of acetic acid to formaldehyde in stream S1 is in the range from 0.75:1 to 1.1:1, the molar ratio of oxygen to the total amount of organic carbon in stream S1 is in the range from 0.02:1 to 0.15:1, the ratio of the volumes of formaldehyde to water in stream S1 is in the range from 0.8:1 to 1.3:1, the space velocity GHSV in the reaction zone is in the range from 1600 to 6500 $h^{-1}$ and the temperature in the reaction zone is in the range from 380 to 400° C.

* * * * *